United States Patent
Bunch et al.

(10) Patent No.: US 9,504,816 B2
(45) Date of Patent: Nov. 29, 2016

(54) MULTI-MODE SYRINGE

(75) Inventors: Jesse Bunch, Silver Spring, MD (US); Abraham Ingber, Rockville, MD (US)

(73) Assignee: SyringeTech LLC, Rockville, MD (US)

( * ) Notice: Subject to any disclaimer, the term of this patent is extended or adjusted under 35 U.S.C. 154(b) by 699 days.

(21) Appl. No.: 12/405,440

(22) Filed: Mar. 17, 2009

(65) Prior Publication Data

US 2009/0234323 A1   Sep. 17, 2009

Related U.S. Application Data

(60) Provisional application No. 61/037,263, filed on Mar. 17, 2008.

(51) Int. Cl.
*A61M 5/00* (2006.01)
*A61M 39/24* (2006.01)
*A61M 5/168* (2006.01)
(Continued)

(52) U.S. Cl.
CPC ......... *A61M 39/24* (2013.01); *A61M 5/16813* (2013.01); *A61M 5/16881* (2013.01); *A61M 5/31511* (2013.01); *A61M 5/3293* (2013.01); *A61M 5/46* (2013.01); *A61M 2039/242* (2013.01); *A61M 2039/244* (2013.01); *A61M 2039/2493* (2013.01)

(58) Field of Classification Search
CPC .......... A61M 5/16881; A61M 39/24; A61M 5/16813; A61M 2039/242; A61M 2039/244; A61M 5/3293; A61M 5/31511; A61M 2039/2493; A61M 5/46

USPC .......... 604/167.02, 110, 192, 198, 237, 207, 604/186–187, 246–247, 201, 95.04, 604/99.02–99.04
See application file for complete search history.

(56) References Cited

U.S. PATENT DOCUMENTS 3,818,907 A * 6/1974 Walton ............................ 604/38
3,949,748 A 4/1976 Malmin
(Continued)

FOREIGN PATENT DOCUMENTS

GB    1 203 098    8/1970
GB    1 210 676    10/1970
(Continued)

OTHER PUBLICATIONS

International Application No. PCT/US2009/037407, Notification of Transmittal of the International Search Report and the Written Opinion of the International Searching Authority, mailed Aug. 18, 2009.
(Continued)

*Primary Examiner* — Bhisma Mehta
*Assistant Examiner* — Amber Stiles
(74) *Attorney, Agent, or Firm* — Fish & Richardson P.C.

(57) ABSTRACT

A syringe cartridge includes a multi-mode device that defines at least two flow regimes having flow rates that differ in response to the same value of a variable. The multi-mode device defines three flow paths. The first flow path allows flow in only a first direction. The second flow path is configured to allow flow below a predetermined rate in a second direction opposite the first direction in response to a variable having a value below a threshold. The third path is configured to allow flow in the second direction at a rate higher than the predetermined rate in response to the variable reaching a value at or above the threshold.

16 Claims, 30 Drawing Sheets

(51) Int. Cl.
*A61M 5/315* (2006.01)
*A61M 5/32* (2006.01)
*A61M 5/46* (2006.01)

(56) References Cited

U.S. PATENT DOCUMENTS

| | | | |
|---|---|---|---|
| 4,403,988 A | | 9/1983 | Binard et al. |
| 4,569,662 A | | 2/1986 | Dragan |
| 4,581,022 A | | 4/1986 | Leonard et al. |
| 4,662,868 A | * | 5/1987 | Cambio, Jr. .................... 604/32 |
| 4,747,824 A | | 5/1988 | Spinello |
| 4,784,637 A | * | 11/1988 | Ryder et al. .................... 604/32 |
| 4,828,547 A | * | 5/1989 | Sahi et al. .................... 604/110 |
| 5,049,135 A | * | 9/1991 | Davis ........................... 604/181 |
| 5,137,528 A | | 8/1992 | Crose |
| 5,139,490 A | | 8/1992 | Vetter et al. |
| 5,180,371 A | | 1/1993 | Spinello |
| 5,221,256 A | | 6/1993 | Mahurkar |
| 5,431,185 A | * | 7/1995 | Shannon et al. ........... 137/512.4 |
| 5,542,933 A | | 8/1996 | Marks |
| 5,690,618 A | | 11/1997 | Smith et al. |
| 5,807,334 A | | 9/1998 | Hodosh et al. |
| 5,944,698 A | | 8/1999 | Fischer et al. |
| 6,056,728 A | | 5/2000 | von Schuckmann |
| 6,083,002 A | | 7/2000 | Martin et al. |
| 6,095,491 A | * | 8/2000 | Kriesel ........................ 251/206 |
| 6,095,814 A | | 8/2000 | Petrich et al. |
| 6,146,354 A | * | 11/2000 | Beil ............................... 604/28 |
| 6,354,603 B1 | | 3/2002 | Villette |
| 6,383,168 B1 | | 5/2002 | Landau et al. |
| 6,432,090 B1 | | 8/2002 | Brunel |
| 6,454,745 B1 | | 9/2002 | Donnan et al. |
| 6,508,792 B2 | | 1/2003 | Szames et al. |
| 6,514,231 B1 | | 2/2003 | Szapiro et al. |
| 6,648,859 B2 | | 11/2003 | Bitdinger et al. |
| 6,719,736 B2 | | 4/2004 | Collins et al. |
| 6,764,471 B2 | | 7/2004 | Lee |
| 6,786,885 B2 | | 9/2004 | Hochman et al. |
| 2001/0007327 A1 | | 7/2001 | Ritsche et al. |
| 2002/0052579 A1 | | 5/2002 | Sogaro |
| 2002/0055720 A1 | | 5/2002 | Hohlfelder et al. |
| 2002/0156431 A1 | * | 10/2002 | Feith et al. .................... 604/247 |
| 2003/0187407 A1 | | 10/2003 | Bills |
| 2003/0195477 A1 | | 10/2003 | Ruben |
| 2003/0212372 A1 | | 11/2003 | Bills et al. |
| 2005/0101913 A1 | | 5/2005 | Hohlfelder et al. |
| 2005/0209555 A1 | | 9/2005 | Middleton et al. |
| 2005/0273079 A1 | | 12/2005 | Hohlfelder et al. |
| 2006/0052753 A1 | | 3/2006 | Mansouri |
| 2006/0079862 A1 | | 4/2006 | Genosar |
| 2007/0250010 A1 | | 10/2007 | Hohlfelder et al. |

FOREIGN PATENT DOCUMENTS

| | | |
|---|---|---|
| JP | 2003-126252 | 5/2003 |
| WO | 01/30423 | 5/2001 |
| WO | 01/30424 | 5/2001 |
| WO | WO2004026377 | 4/2004 |
| WO | 2006/005206 | 1/2006 |
| WO | WO 2006/005206 | 1/2006 |
| WO | WO2006014339 | 2/2006 |
| WO | 2006/058435 | 6/2006 |
| WO | 2006/090509 | 8/2006 |
| WO | WO 2006/090509 | 8/2006 |

OTHER PUBLICATIONS

"Fundamentals of Dental Assisting," available at http://64.78.42.182/sweethaven/MedTech/Dental/DentAssist/DentAssist01_TXT.asp?frame=0203, Aug. 13, 2007, 2 pages.

* cited by examiner

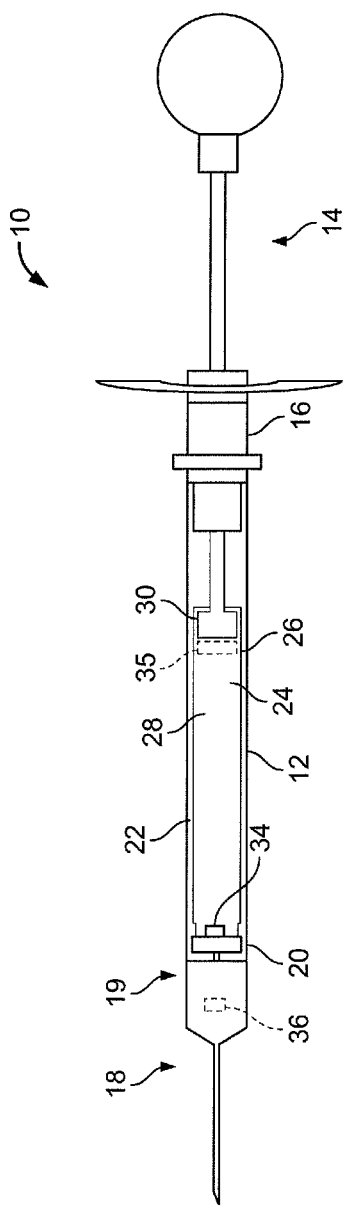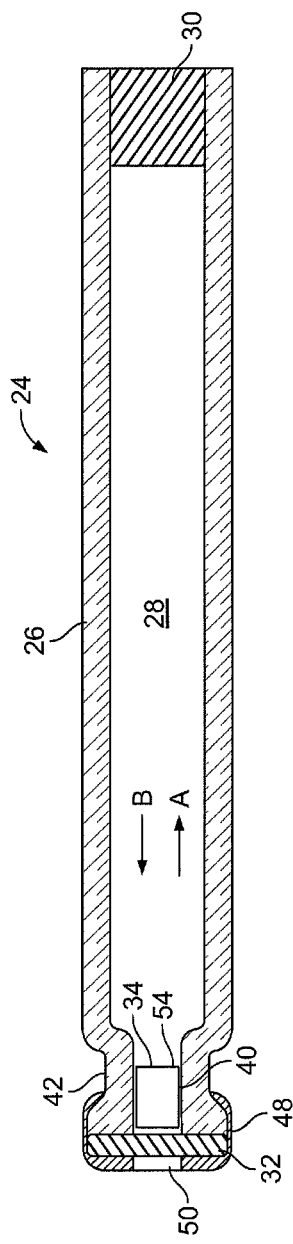

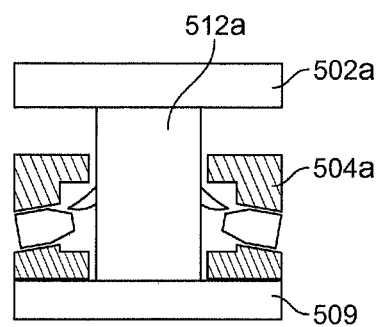 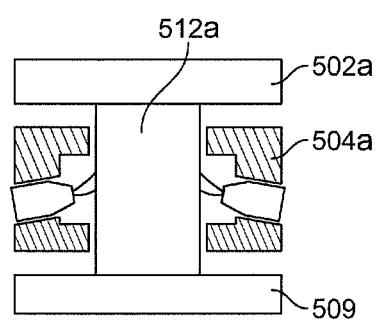
FIG. 11D          FIG. 11E
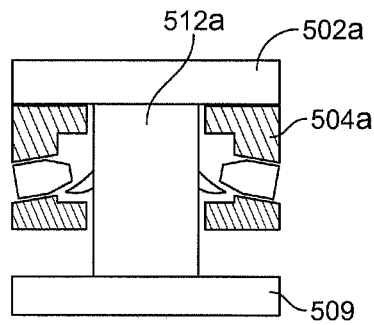
FIG. 11F

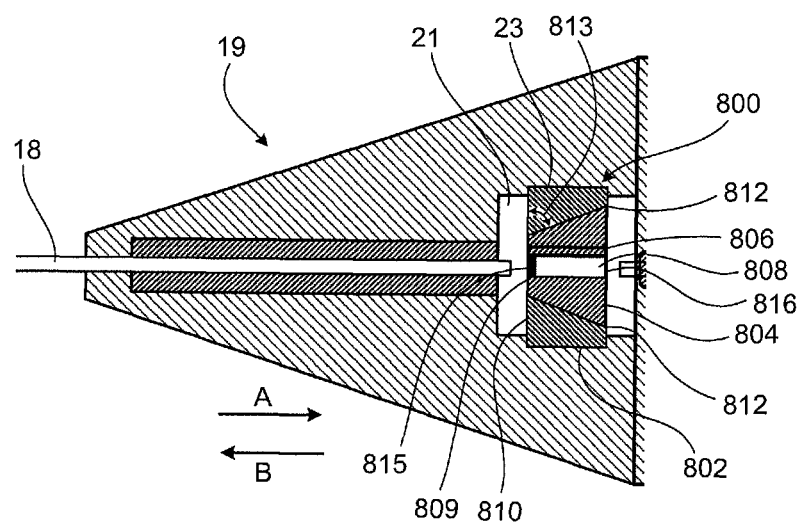
FIG. 15B
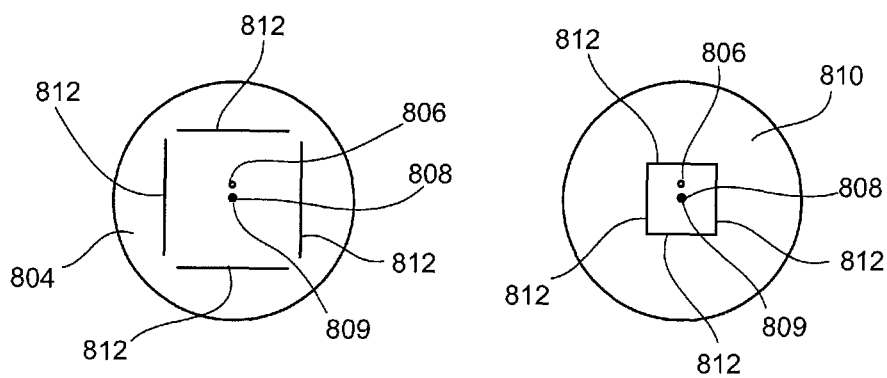
FIG. 15C
FIG. 15D

MULTI-MODE SYRINGE

CROSS-REFERENCE TO RELATED APPLICATION

This application claims priority from U.S. Application Ser. No. 61/037,263, filed on Mar. 17, 2008.

BACKGROUND

The discomfort associated with the injection of anesthetics results from the pressure of the incoming fluid. To minimize the discomfort, the anesthetic can be injected very slowly at first to numb the nerves and tissue at the point of the injection. The fluids can then be introduced at a higher rate without discomfort.

Known devices include motor driven syringes and microprocessor-controlled pumps. For example, U.S. Pat. No. 5,807,334 employs a motor built into the syringe to depress the plunger of a syringe cartridge. Multiple gears provide slow flow rates and faster flow rates. A number of devices employ a microprocessor-controlled pump to control anesthetic flow rates. In one example of a microprocessor-controlled pump, the pump is in a unit distant from the hand held needle-bearing device. Tubing is then necessary to transmit the fluid from the pump to the needle. In another example, U.S. Patent App. Pub. No. 2001/0007327 A1 employs repeated strokes on an altered syringe cartridge to meter the flow of anesthetic.

SUMMARY

It is difficult for most practitioners to control the force applied to a conventional syringe well enough to successfully implement a pain-minimizing method. The disclosed embodiments provide multiple modes of operation required for minimal injection discomfort while permitting the practitioner to continue using his/her familiar syringe. The functional anesthetic capacity and external dimensions of the syringe remains unchanged.

The modes can be directly controlled by the value(s) of one or more applied force-related variables, for example, force, impact, impulse, or some combinations thereof The modes can be controlled by the value(s) of one or more pressure-related variables in a medium being dispensed resulting from the value of one or more of the applied force-related variables. Below a pre-determined threshold value of the force-related or pressure-related variable, the flow rate of the medium is limited to a rate slow enough to maximize the patient's comfort. Once the pre-determined threshold value of the force-related or pressure-related variable is reached, the mode changes to one of a conventional relationship between the force applied to the medium and the flow rate of the medium. The multi-mode device may be included in a syringe cartridge or inserted into the head of a syringe to provide the multiple mode capability. The device can employ, for example, mechanical, fluidic, and/or microfluidic means to provide the multi-mode capability.

A valve in the insert permits body fluids to enter the syringe cartridge when the practitioner applies a negative force to the syringe's plunger. The practitioner can employ this to determine if a blood vessel or artery has been entered. An opening in the insert provides very slow anesthetic flow rates until a larger valve opens, permitting a range of flow rates, including high flow rates. The opening of the larger valve can be triggered by reaching a threshold value of a pressure-related variable in the syringe cartridge resulting from the value of a force-related variable applied to the syringe's plunger. That value of the force-related variable is applied by the practitioner. Alternatively, the opening of the larger valve can be triggered by the amount of anesthetic already dispensed or, directly or indirectly via an electric, magnetic, electronic, or other signal.

According to one aspect, a syringe cartridge includes a housing configured for removable placement within a syringe barrel, and a plunger, a seal, and a multi-mode device each attached to the housing for removable placement therewith.

According to another aspect, a syringe includes a barrel for containing a medium, a plunger for applying a force-related variable to the medium, and a multi-mode device incorporated within the barrel and/or attached to the plunger. The multi-mode device defines at least two flow regimes having flow rates that differ in response to the same value of a variable. In embodiments of this aspect, the syringe includes a housing within the barrel for containing the medium, and the housing is configured for removable placement within the barrel.

According to another aspect, a syringe includes a needle hilt, a barrel for containing a medium, a plunger for applying a force-related variable to the medium, and a multi-mode device incorporated within the needle hilt. The multi-mode device defines at least two flow regimes having flow rates that differ in response to the same value of a variable.

According to another aspect, a multi-mode syringe device includes a body sized for placement within a syringe. The body defines three flow paths. The first flow path includes a one-way valve configured to allow flow in only a first direction. The second flow path is configured to allow flow below a predetermined rate in a second direction opposite the first direction in response to a variable having a value below a threshold. The third path is configured to allow flow in the second direction at a rate higher than the predetermined rate in response to the variable reaching a value at or above the threshold.

According to another aspect, a method includes applying a force by hand to a syringe plunger to cause flow of medium from the syringe below a predetermined rate in a first flow regime in response to a variable having a value below a threshold, and applying a force by hand to the syringe plunger to cause a change in flow of medium from the syringe above the predetermined rate in a second flow regime in response to the variable reaching a value at or above the threshold. The two flow regimes have flow rates that differ in response to the same value of the variable.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is an illustration of a multi-mode syringe.

FIG. 2 is a cross-sectional side view of a syringe cartridge including a multi-mode, variable flow device.

FIGS. 11D-11F are cross-sectional side views of an additional alternative embodiment of a multi-mode, variable flow device associated with a plunger of a syringe cartridge and isolated from the anesthetic fluid.

FIG. 15B is an exploded side views of the multi-mode, variable flow device of FIG. 15A, FIG. 15C is a proximal view of the multi-mode, variable flow device of FIG. 15A.

FIG. 15D is a distal view of the multi-mode, variable flow device of FIG. 15A.

DETAILED DESCRIPTION

Figure 3A:
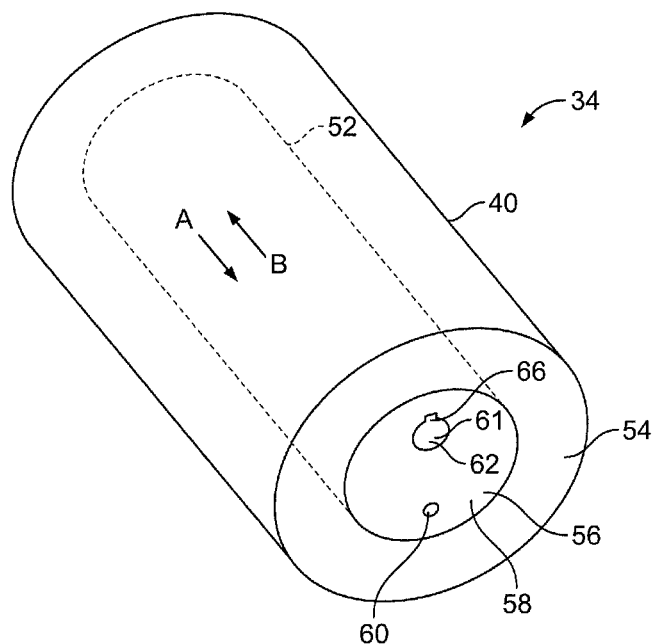
FIGS. 3A and 3B are perspective views of the multi-mode, variable flow device of FIG. 2.

Referring to FIG. 1, a syringe assembly 10 includes a barrel 12, a plunger assembly 14 located at a first, proximal end 16 of the barrel 12, and a needle assembly 18 extending through a needle hilt 19 located at the opposite, distal end 20 of the barrel 12. The barrel 12 defines a chamber 22 within which is removably received a cartridge 24 having a housing 26 containing a medium 28 to be delivered to a patient, for example, anesthetic for use during a dental procedure. Referring also to FIG. 2, attached to the housing 26 for removable placement therewith within the barrel 12 is a plunger 30, a seal 32, and a multi-mode, variable flow device 34. Alternatively, a multi-mode device 35 can be positioned near, against, or integral to the plunger 30, or a multi-mode device 36 can be positioned in or integral to the needle hilt 19. When assembled, the plunger assembly 14 pierces the plunger 30, and the needle assembly 18 pierces the seal 32 such that actuation of the plunger assembly 14 advances the cartridge plunger 30 forcing the medium 28 through the needle assembly 18 to the patient. As discussed below, the multi-mode devices 34-36 act to automatically limit the initial flow rate of anesthetic into the patient to minimize the level of pain experienced by the patient prior to the onset of numbing.

The multi-mode device 34 includes a cylindrical member 40 sized to be received within a distal region 42 of the housing 26 by, for example, a friction fit, adhesive, and/or pins. The distal region 42 of the housing 26 is closed off by the seal 32, which is secured in place by a cap 48. The cap 48 has an opening 50 through which the needle assembly 18 extends to puncture the seal 32.

Figure 3B:
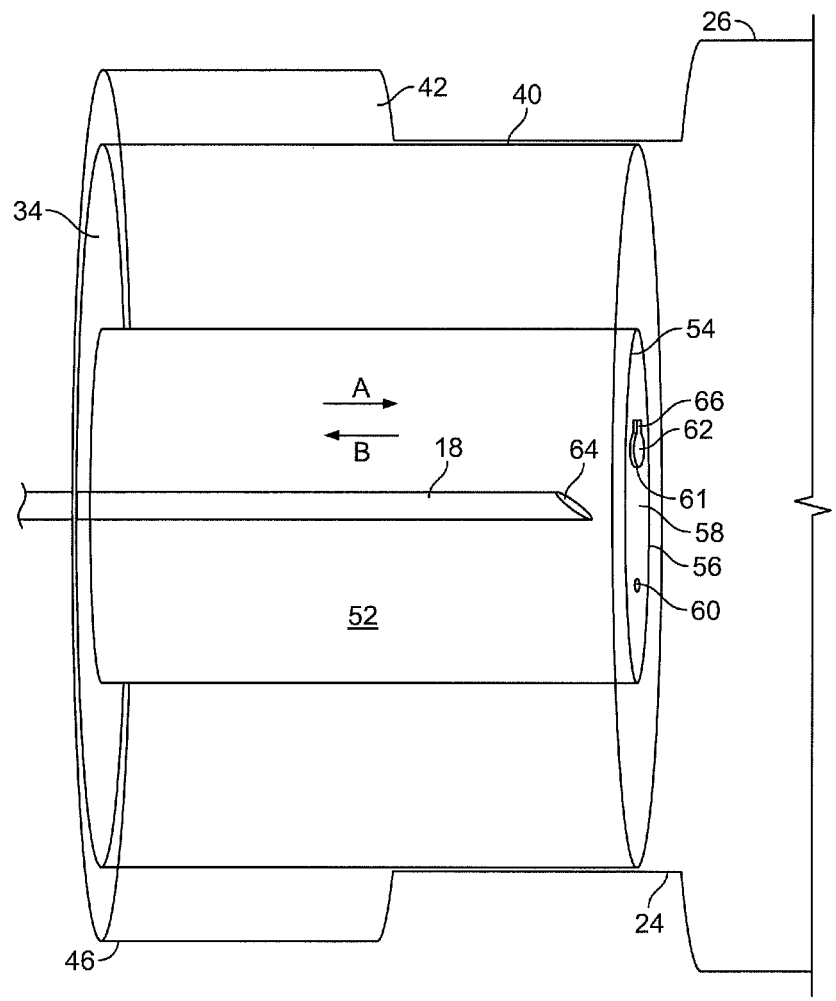

Referring to FIGS. 3A and 3B, the cylindrical member 40 of the multi-mode device 34 defines a chamber 52 for delivery of anesthetic therethrough. The cylindrical member 40 has a front, proximal face 54 defining an opening 56 to the chamber 52. Across the opening 56 is a membrane 58. The membrane 58 defines a first opening 60 having a diameter in the range of 5 to 50 micrometers. The optimal value of the diameter of the first opening 60 within this range depends on a number of variables including the cartridge plunger's friction, the distance between the first opening 60 and the axis of the cartridge, the distance between the first opening 60 and the back entrance of the needle, the thickness of the membrane 58, the maximum acceptable pressure at the site of injection, and the value chosen for the differential pressure across the membrane at the transition between the second and third phases, discussed below.

Figure 3C:
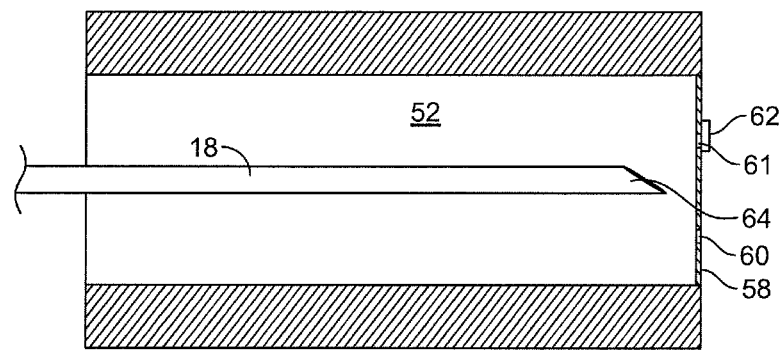
FIGS. 3C and 3D are cross-sectional side views of the multi-mode, variable flow device of FIG. 2.
Figure 3D:
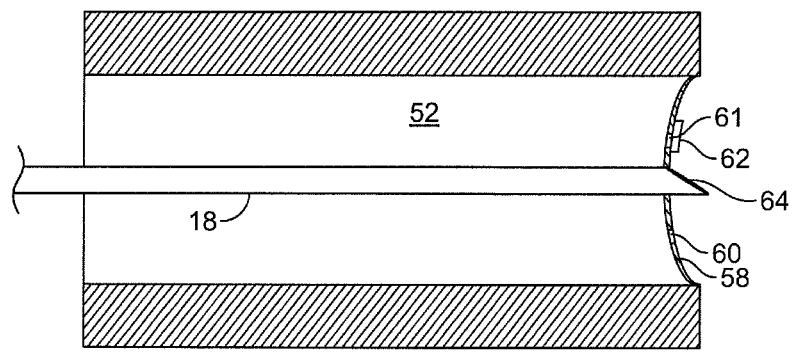

The membrane 58 also defines a second opening 61 having a diameter about the same as or greater than the inner diameter of the needle of needle assembly 18, and includes a one-way valve 62 that, when closed, covers opening 61. The one-way valve 62 is attached to the membrane 58 by a hinge 66 and only allows flow through opening 61 in a reverse direction, arrow A. As illustrated in FIGS. 3B and 3C, when the needle assembly 18 is attached to the barrel 12 piercing the seal 32, the needle assembly 18 extends into the chamber 52 with a sharp tip 64 of the needle assembly 18 positioned near the membrane 58. The membrane 58 distorts when a net forward pressure differential across membrane 58 is applied by the cartridge plunger 30. When the value of a net forward pressure-related variable across the membrane 58 is at or above a threshold, for example, 150 to 350 kPa, the membrane 58 moves against the sharp tip 64 of the needle assembly 18 and is punctured (FIG. 3D). The sharp tip 64 tears the membrane 58 or penetrates through the membrane 58 depending on the characteristics and dimensions of the membrane 58. The membrane 58 can be perforated to predefine the shape of the tear and/or the pressure causing the tear. The differential pressure across the membrane 58 at the transition from the second to third phase can vary outside this range depending upon the frictional force applied by the cartridge plunger.

The multi-mode device 34 defines three flow paths. The first flow path is through one-way valve 62 when the operator applies a back force to the cartridge plunger 30 resulting in a net back pressure differential across membrane 58. The second flow path is through opening 60, which allows flow in a forward direction, arrow B, when a variable, here the operator applied forward value of a force-related variable placed on the cartridge plunger 30 resulting in a pressure-related variable across membrane 58, is below the threshold. The third flow path is through the punctured membrane 58, which begins when the operator applies a forward value of a force-related variable to the cartridge plunger 30 resulting in a pressure-related variable across membrane 58 at or above the threshold.

There are thus three distinct possible phases of flow: 1) reverse flow through the first flow path, which permits the operator to check for proper placement of the needle; 2) forward flow below a predetermined rate, for example, less than 1 cc per minute, when the applied pressure-related variable across membrane 58 is below the threshold, which automatically enables the operator to numb the tissue while minimizing pain and discomfort to the patient; and 3) forward flow that can reach rates above the predetermined rate initiated by an applied pressure-related variable across membrane 58 at or above the threshold level, which permits the operator to complete the injection with the flow characteristics of the syringe being that of a typical syringe having a cartridge without a multi-mode device. The forward force applied to the cartridge plunger 30 acts to produce a pressure differential across the membrane 58 to close the one-way valve 62.

Figure 4:
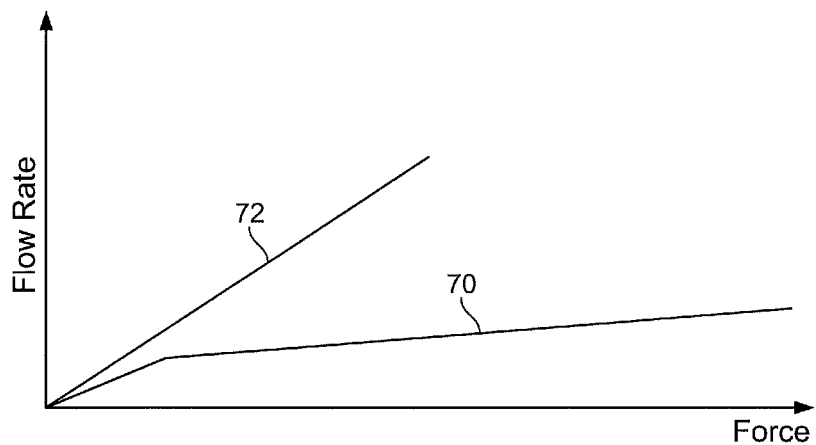
FIG. 4 is a flow rate diagram for the multi-mode, variable flow device of FIG. 2.

Referring to FIG. 4, the flow regimes within the second and third phases 70, 72, respectively, differ. For the same value of the variable, for example, the net applied force, the flow rate in the third phase 72 is higher than the flow rate in the second phase 70. Thus, the second phase 70 is not as responsive to the applied force as is the third phase. The third phase 72 is limited by the characteristics of the needle assembly 18, as in a conventional syringe without a multi-mode device 34, whereas the second phase 70 is limited by the size of the opening 60 of the multi-mode device 34. While the flow regimes within the second and third phases 70, 72, respectively, differ, they need not be linear as illustrated, but can vary non-linearly within a phase.

Figure 5A:
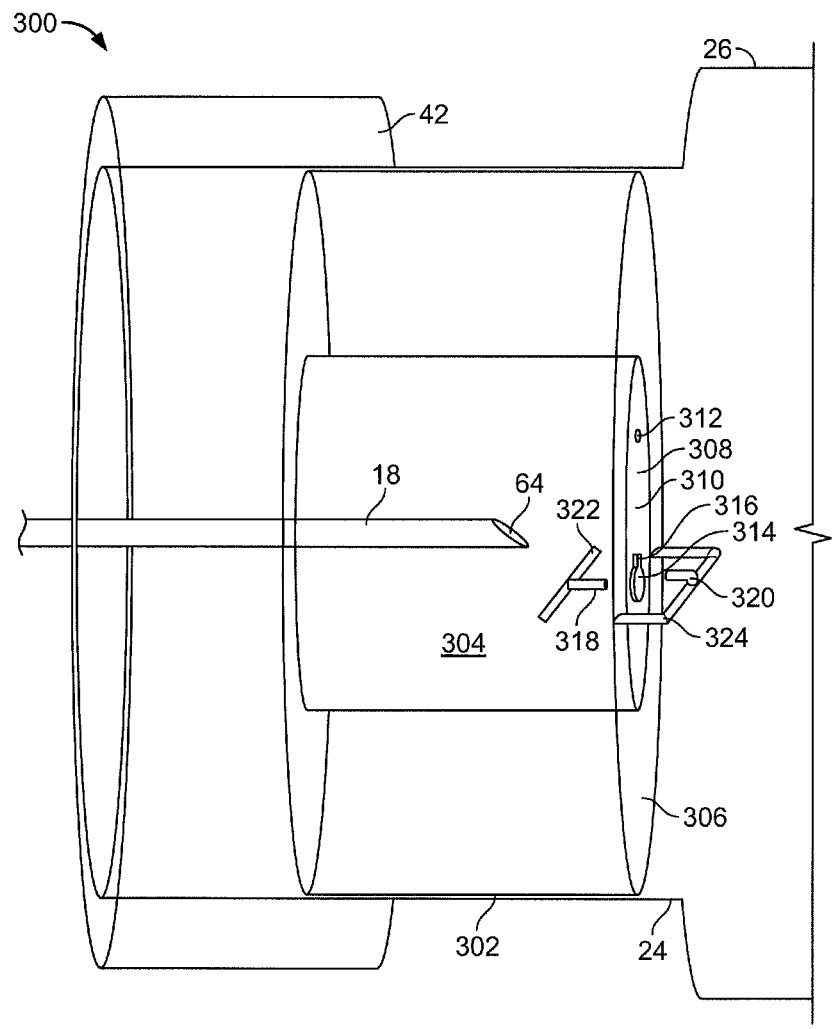
FIG. 5A is a perspective view of an alternative embodiment of a multi-mode, variable flow device.
Figure 5B:
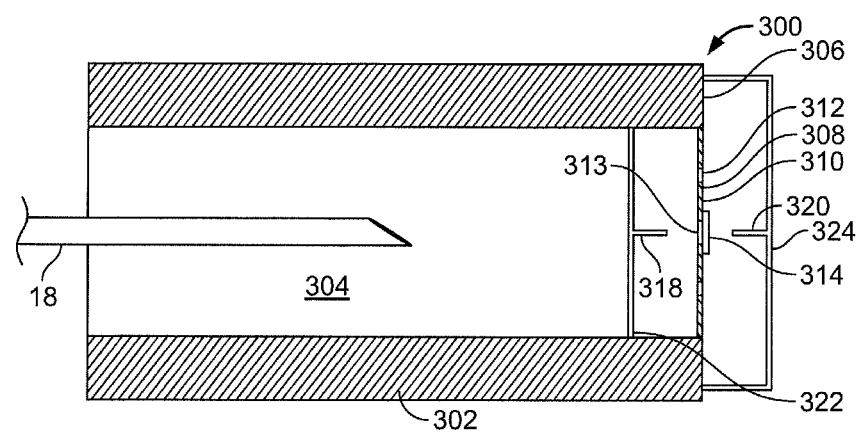
FIG. 5B is a cross-sectional side view of the multi-mode, variable flow device of FIG. 5A.

Referring to FIGS. 5A and 5B, in another alternative embodiment, a multi-mode device 300 includes a cylindrical member 302 defining a chamber 304 for delivery of anesthetic therethrough. The multi-mode device 300 has a front, proximal face 306 defining an opening 308 to the chamber 304. Across the opening 308 is a membrane 310. The membrane 310 defines an opening 312 and an opening 313. The flow of anesthetic through opening 313 can be blocked or unblocked by a bi-stable valve 314. The bi-stable valve 314 is attached to the membrane 310 by a hinge 316. The bi-stable valve 314 is controlled by a valve opener 318 connected to a valve opener support frame 322, and a valve closer 320 connected to a valve closer support frame 324. The valve opener support frame 322 is attached to the inner wall of the chamber 304 and the valve closer support frame 324 is attached to the cylindrical member 302. The bi-stable valve 314 can move to a partially open position toward closer 320 under a back pressure resulting from an applied negative force, from which the valve will automatically close when the back pressure differential across the membrane 310 is reduced by the aspiration flow, and can move to a stable open position, as described further below. (Closer 320 can prevent the bi-stable valve from becoming stably open at this time.) The stable open position of the bi-stable valve 314 is achieved, for example, by an elastic band 326 (FIG. 5D) extending between the hinge 316 and the bi-stable valve 314.

Figure 5C:
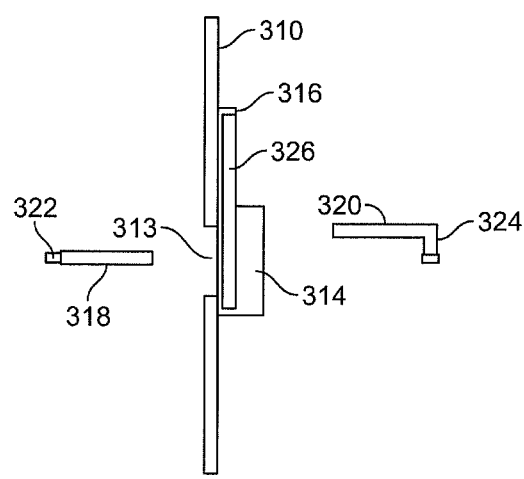
FIGS. 5C-5E are exploded side views of the multi-mode, variable flow device of FIG. 5A.
Figure 5D:
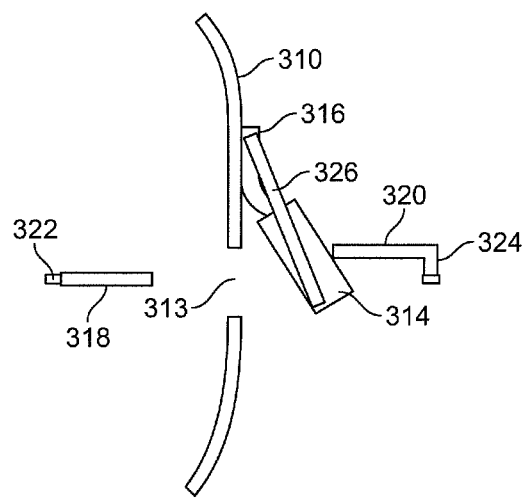
Figure 5E:
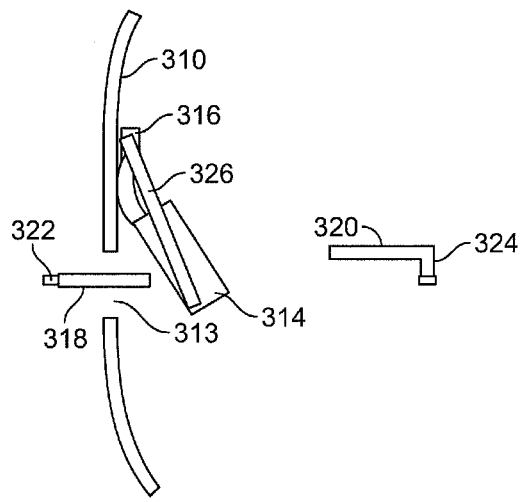

Before force is first applied to the cartridge plunger 30, the bi-stable valve 314 is closed (FIG. 5C). When the operator applies back force to the cartridge plunger 30, sufficient for it to move, a first flow path is created through the bi-stable valve 314, which is in its partially open position (FIG. 5D), that is, the valve has moved toward or up against closer 320 but short of its stable open position. When the back force ceases, the pressure differential across membrane 310 is reduced due to the aspiration flow, the valve 314 returns to the position of FIG. 5C. When the operator applies forward force to the cartridge plunger 30 resulting in a below a threshold pressure, the bi-stable valve 314 remains closed and the second flow path is through the opening 312. The third flow path is through the bi-stable valve 314. When the operator applies a forward force to the cartridge plunger 30 resulting in a forward value of a variable related to the pressure differential across membrane 310 at or above the threshold, the membrane 310 distorts and moves the bi-stable valve 314 against the valve opener 318 (FIG. 5E). The valve opener 318 pushes the bi-stable valve 314 to a stably open mode. Because the bi-stable valve 314 is stably open, it remains open after the pressure differential across membrane 310 is lessened and the membrane 310 returns to its original position. To close the valve, the operator applies a negative force to the cartridge plunger 30 resulting in a negative value of a variable related to the pressure differential across membrane 310 such that the membrane 310 moves the bi-stable valve 314 against the valve closer 320 (FIG. 5D). The valve closer 320 pushes the bi-stable valve 314 closed (FIG. 5C). This returns the cartridge to a state where a below threshold forward cartridge plunger force will result in second phase response mode and a reverse cartridge plunger force will result in first phase fluid flow.

The bi-stable valve can advantageously eliminate pressure differences between the two sides of the membrane 310 that can result from insertion of the cartridge 24 into the barrel 12 of the syringe assembly 10 during manufacture. The burst of flow that occurs from triggering the third phase can be tailored by designing the bi-stable valve to open at a pre-defined rate. The bi-stable valve can be designed to open slowly to reduce the trigger flow, or the bi-stable valve can be completely removed or altered if a microfluidic circuit is used.

Figure 6A:
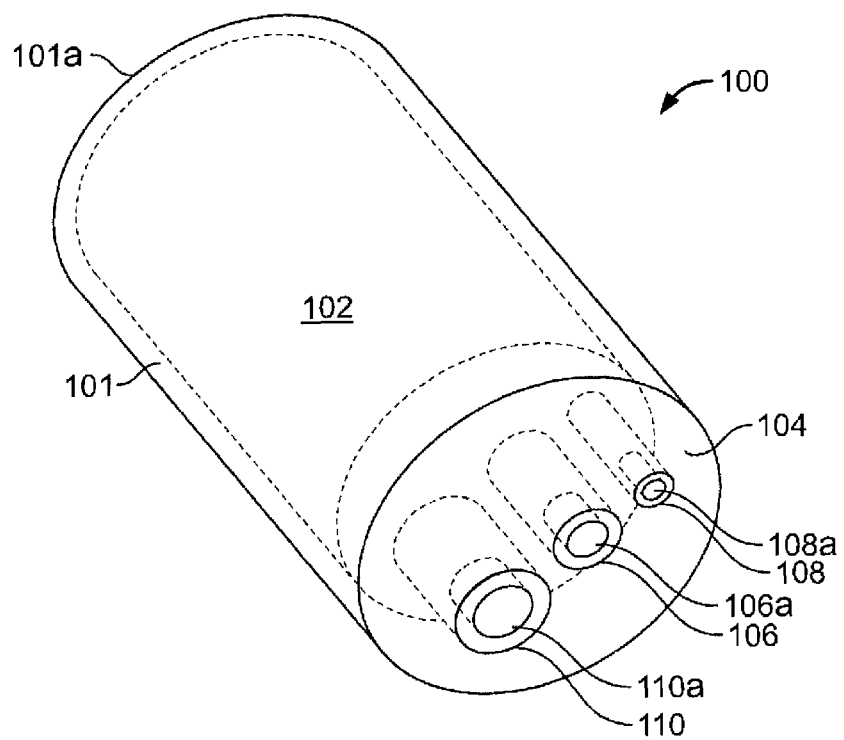
FIGS. 6A and 6B are perspective views of an additional alternative embodiment of a multi-mode, variable flow device.
Figure 7A:
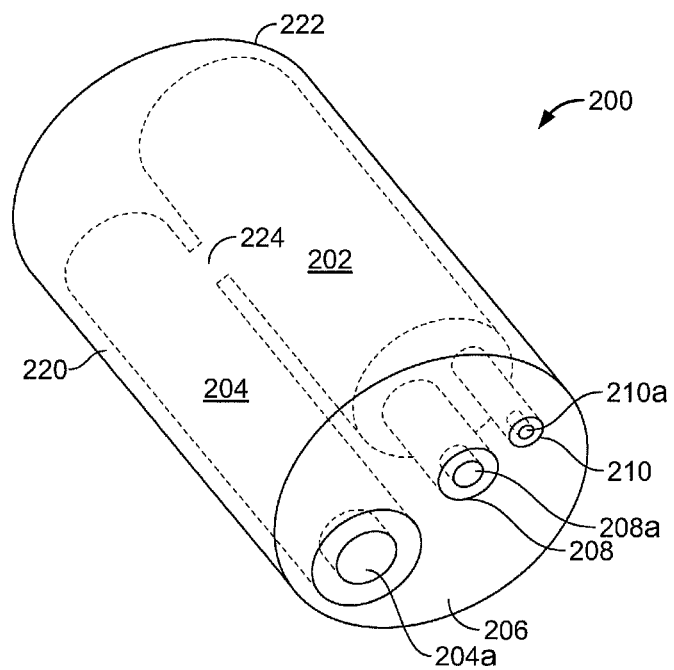
FIGS. 7A and 7B are perspective views of an additional alternative embodiment of a multi-mode, variable flow device.

FIGS. 6A and 7A illustrate other configurations for the cylindrical member of the multi-mode device. Flow regulation through the flow paths can be provided by the methods described herein and by "fluidic" and "micro-fluidic" circuits. These employ fluid dynamics to achieve analogs to electronic and micro-electronic circuitry employing and controlling the flow of fluids instead of electrons. The holes and chambers for flow can number only 2 or 1, depending upon the implementation. For example, a micro-fluidic circuit can perform the function of regulating all three phases and the transition between them.

Figure 6C:
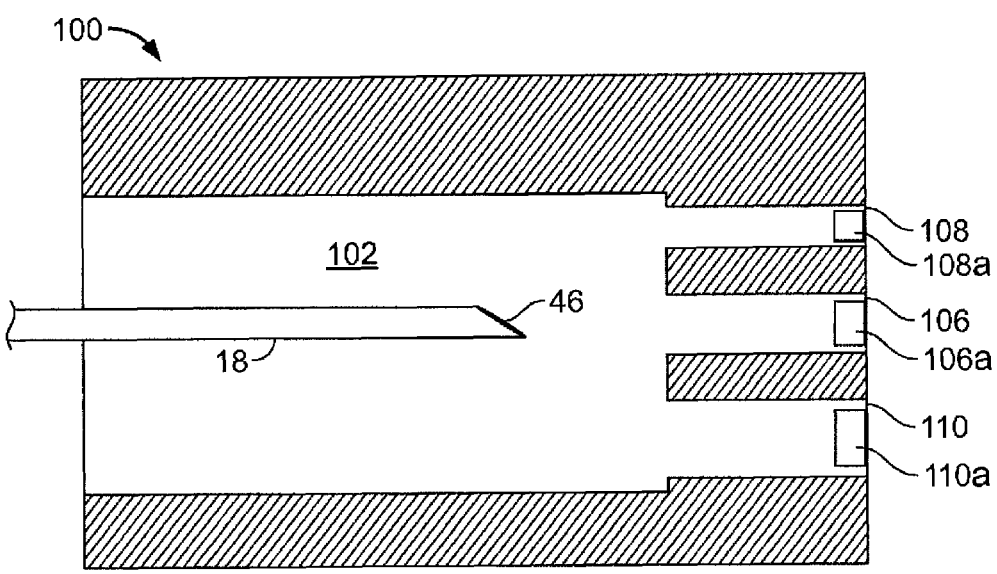
FIG. 6C is a cross-sectional side view of the multi-mode, variable flow device of FIGS. 6A and 6B.
Figure 6B:
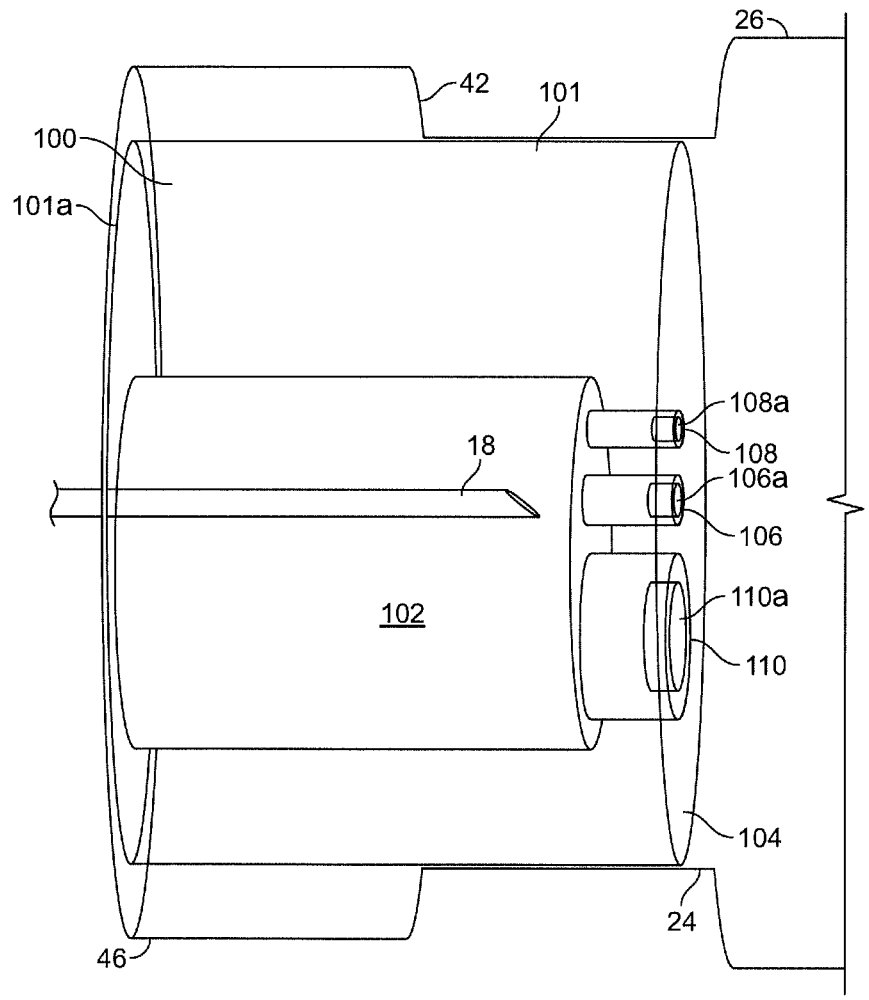

Referring to FIGS. 6A-6C, in an alternative embodiment, a multi-mode device 100 includes a cylindrical member 101 defining a chamber 102 extending from the distal end 101 a of the cylindrical member 101 partially through the multi-mode device 100 for delivery of anesthetic therethrough. The multi-mode device 100 has a front, proximal face 104 defining three through holes, 106, 108, and 110, extending through the front face 104 to the chamber 102 for flow of anesthetic therethrough. The three through holes can differ in diameter, and each of the through holes 106, 108, and 110 includes a means 106a, 108a, 118a to provide flow regulation through the flow paths, as discussed above.

The first flow path is through the hole 106, which can be initially open or can be initially closed, opening when negative pressure is applied across the multi-mode device 100. The second flow path is through the hole 108, which may be initially open, to assist in the back flow through hole 106, or initially closed, opening when a positive value of a variable related to the pressure differential across multi-mode device 100 below the threshold is applied. The third flow path is through the opening 110, which is initially closed, opening when a positive value of a variable related to the pressure differential across multi-mode device 100 at or above the threshold is applied. While the flow paths through holes 108 and 110 are shown as distinct paths in FIG. 6A, the flow paths can be arranged such that the second flow path is a sub-part of the third flow path, for example, the second flow path is a partial opening of a valve and the third flow path is further opening of the valve. Likewise, the first flow path may be the same as the third, only in the opposite direction.

Figure 7C:
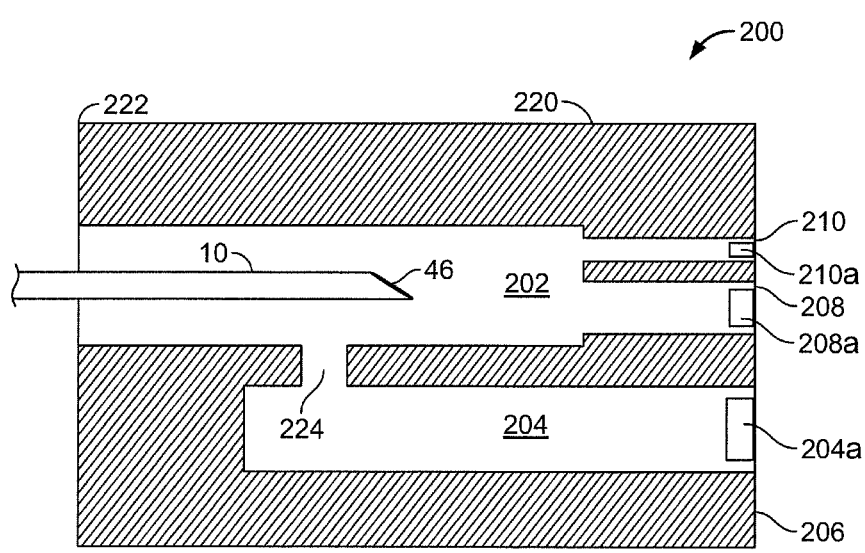
FIG. 7C is a cross-sectional side view of the multi-mode, variable flow device of FIGS. 7A and 7B.
Figure 7B:
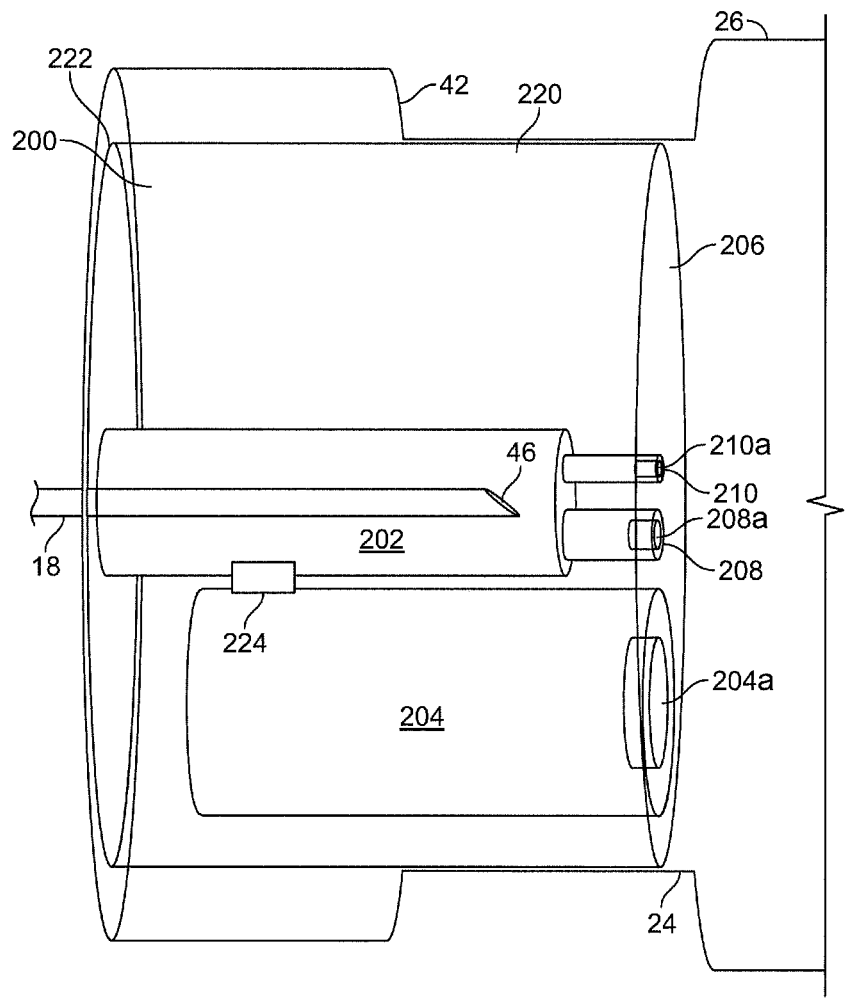

Referring to FIGS. 7A-7C, in another alternative embodiment, a multi-mode device 200 includes a cylindrical member 220 defining a first chamber 202, a second chamber 204, and a fluid path 224 connecting the chambers 202, 204. The first chamber 202 extends at least partially through the multi-mode device 200 from the distal end 222, and the second chamber 204 extends partially through the multi-mode device 200 from the front, proximal face 206. The front face 206 defines two through holes of different diameters, 208 and 210 that extend from the front face 206 to the chamber 202. Each of the through holes 208 and 210 and chamber 204 includes a means 208a, 210a, 204a to provide flow regulation through the flow paths, as discussed above.

The embodiments illustrated in FIGS. 6A-6C and FIGS. 7A-7C can be designed to be reversible from third phase operation back to first phase and/or second phase operation.

In embodiments in which the first flow path is covered by a membrane, the reverse flow is caused by the operator drawing back on the plunger 30 stretching the membrane. When the operator releases the negative force applied to the plunger 30, the membrane returns to its original shape, pushing at least some of the volume drawn in during aspiration out of the cartridge.

Figure 8:
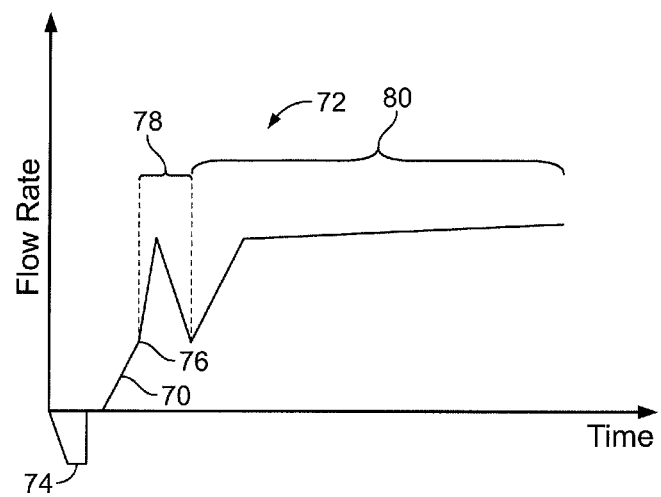
FIGS. 8 and 9 illustrate typical injection profiles.

Referring to FIG. 8, a typical injection profile over time for a multi-mode device includes a first phase flow 74, followed by a second phase flow 70. The operator initiates the transition from the second phase to the third phase by increasing the value of variable related to the applied pressure across the multi-mode device to a value at or above the threshold at 76. This is followed by a brief burst of flow at 78 in the third phase 72 due to the sudden pressure release, which is followed by a period of flow in the third phase 72 that is the standard cartridge flow response 80 over time.

Figure 9:
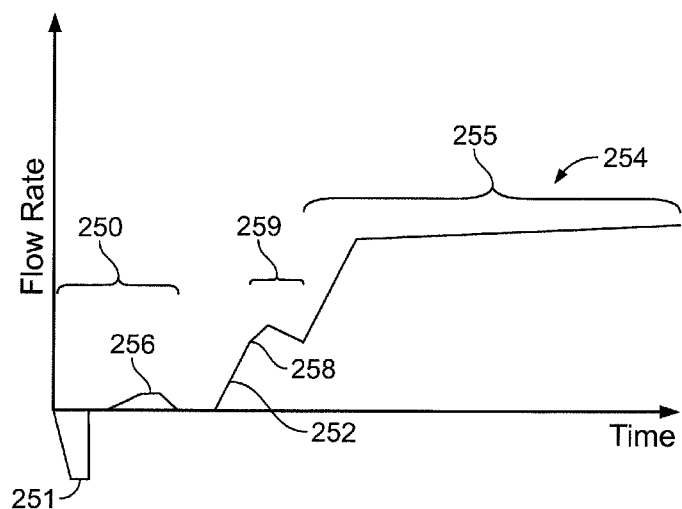

Referring to FIG. 9, a typical injection profile over time for a membrane-based multi-mode device includes a first phase flow 250 that includes a reverse flow stage 251 and a forward flow stage 256 due to rebound of the membrane covering the first flow path, followed by a second phase flow 252. The operator initiates the transition from the second phase to the third phase by increasing the variable related to the pressure across the membrane to a value at or above the threshold value at 258. This is followed by a brief burst of flow at 259 in the third phase 254 due to the increased pressure differential across the multi-mode device, which is followed by a period of flow in the third phase 254 that is the standard cartridge flow response 255 over time. The burst of flow that occurs at the transition from the second phase to the third phase can be tailored by controlling/limiting the rate of membrane tearing, and/or can be reduced by reinforcing the area of the membrane where the needle penetrates the membrane. The rebound and the transition burst of flow can be eliminated in embodiments employing fluidic or micro-fluidic components.

Figure 10A:
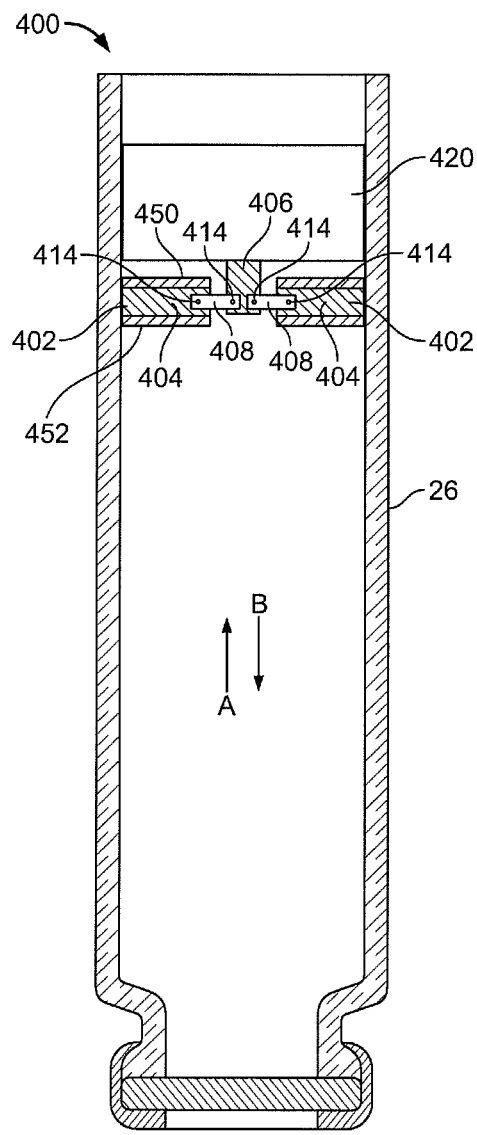
FIGS. 10A, 10C, and 10D are cross-sectional side views of a multi-mode, variable flow device associated with a plunger of a syringe cartridge.
Figure 10B:
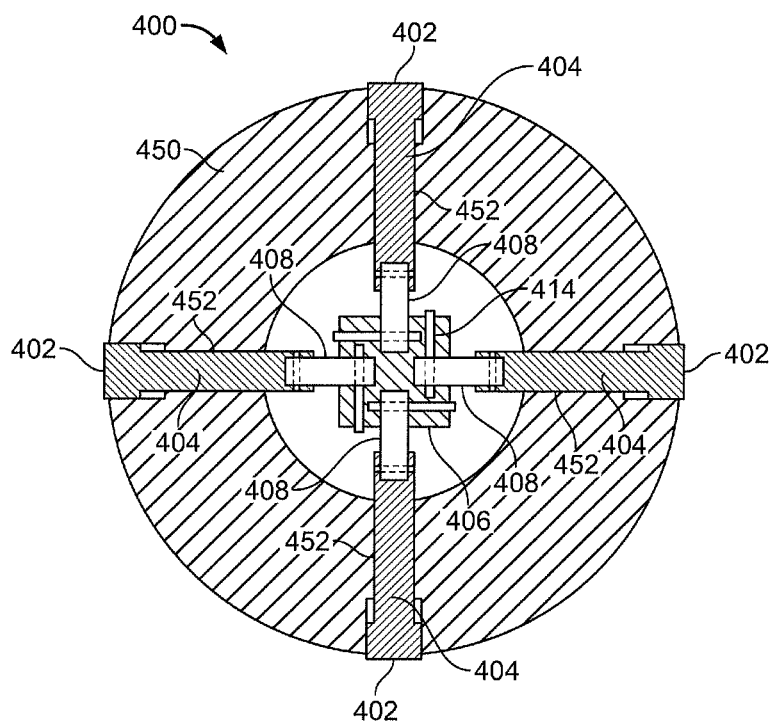
FIG. 10B is a cross-sectional view through the multi-mode, variable flow device of FIGS. 10A, 10C, and 10D.

Rather than positioning the multi-mode device at the distal end of the cartridge, the multi-mode device can be positioned near, against, or integral to the cartridge plunger where the multi-mode device is directly acted upon by the cartridge plunger. Referring to FIGS. 10A and 10B, a multi-mode device 400 is attached to the cartridge plunger 420 by a plunger extension 406. The multi-mode device 400 includes a disk 450 defining at least one slot 452 (here four slots are shown). The disk 450 resists its motion during all phases due to the friction it has with the cartridge housing 26. Within each slot 452 is housed a bar 404 terminating in a friction head 402. The bars 404 are connected to the plunger extension 406 via hinges 408 and pins 414. When the operator moves the plunger 420, the plunger extension 406 is also moved and acts on the hinges 408 to slide the bars 404 within the slots 452. With the bars 404 positioned as shown in FIG. 10A, with the friction heads 402 against the cartridge housing 26, there is a greater resistance to sliding of the plunger 420 within the cartridge housing 26. With the bars 404 positioned as shown in FIGS. 10C and 10D, with the friction heads 402 spaced from the cartridge housing 26, there is less resistance to sliding of the plunger 420 within the cartridge housing 26.

The multi-mode device 400 defines three phases of flow. The first phase allows flow in a reverse direction, arrow A, when the operator applies a back force to the cartridge plunger 420. Referring to FIG. 10C, as the operator applies back force to the cartridge plunger 420, the plunger extension 406 pulls the hinges 408, which slides each friction bar 404 inward such that friction heads 402 are spaced from the cartridge housing 26. The flow characteristics of the syringe are now nearly identical to those of an unaltered cartridge.

Referring again to FIG. 10A, the second phase allows flow in a forward direction, arrow B, when the operator applies a forward value of a force-related variable below the threshold value to the cartridge plunger 420. When the operator applies a forward value of the force-related variable below the threshold value to the cartridge plunger 420, the plunger extension 406 pushes the hinges 408, which slides each friction bar 404 outward such that friction heads 402 move against the cartridge housing 26 (FIG. 10A). In the second phase, the increased friction acts to reduce the flow rate in response to a given operator-applied force as compared to a standard cartridge. Referring to FIG. 10D, the third phase is entered when the operator applies a forward value of the force-related variable at or above the threshold to the cartridge plunger 420. As the forward value of the force-related variable applied to the cartridge plunger 420 reaches the threshold, the plunger extension 406 pushes the hinges 408 downward, which slides each friction bar 404 inward, such that the multi-mode device 400 enters the third phase that allows flows in a forward direction, arrow B and has properties nearly identical to an unaltered cartridge.

The friction heads 402 are made from, or are covered with, a material whose static and kinetic coefficients of friction are similar to or greater than those of the cartridge plunger 420. For example, the friction heads 402 can be made from the same material as the cartridge plunger 420.

Figure 10E:
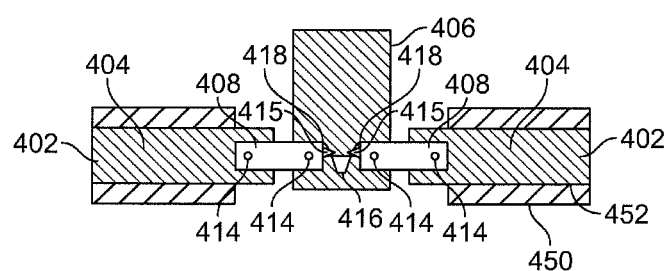
FIG. 10E is an exploded side view of the multi-mode, variable flow device of FIGS. 10A, 10C, and 10D.
Figure 10C:
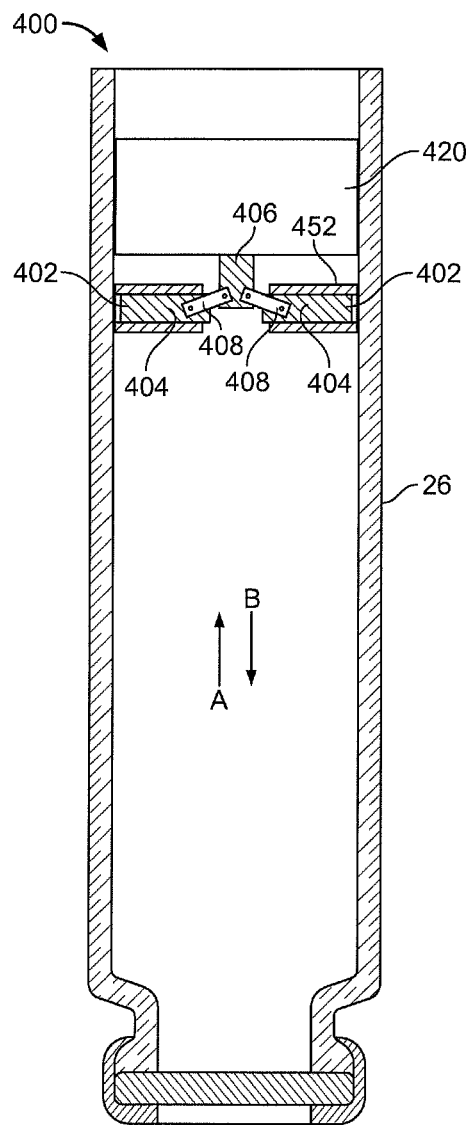
Figure 10D:
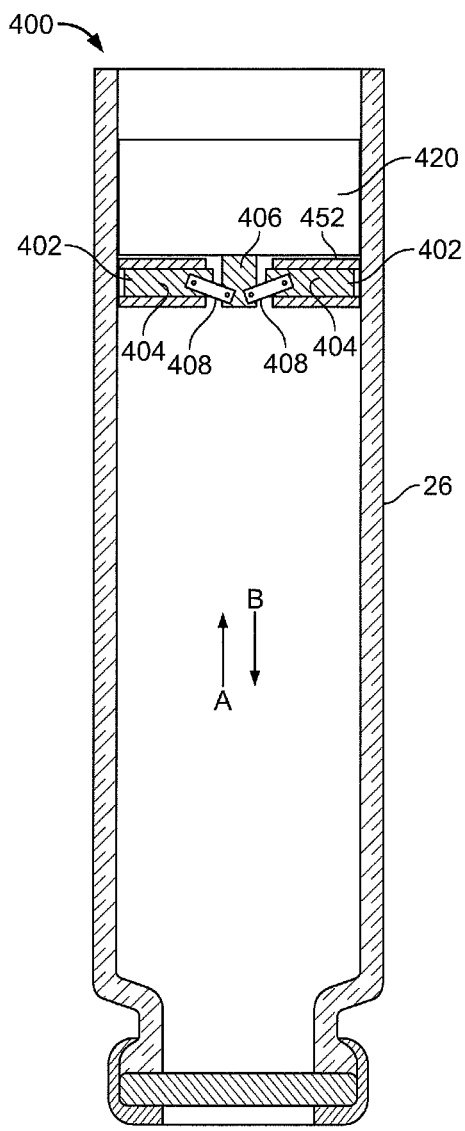

Referring to FIG. 10E, the hinges 408 can include tabs 415 affixed to their inner ends 418, and the plunger extension 406 can include a tab block 416 affixed to it. The tab block 416 of the plunger extension 406 acts against the rotation of the hinges 408 keeping the friction bars 404 pressed against the housing 26 to maintain the second flow rate phase over a broader range of forces applied to the cartridge plunger 420. Once the value of the forward force-related variable applied to the cartridge plunger 420 is at or greater than the threshold, the tabs 415 bend enough to allow the hinges 408 to rotate enough for the tabs 415 to clear the tab block 416, thereby pulling the friction bars 404 inward and allowing the start of the third phase.

The multi-mode device 400 can be configured to easily make the transition from the third phase back to the second phase by applying a backward force to the cartridge plunger 420. Referring to FIG. 10E, the tab block 416 is configured such that tabs 415 bend easily under the backward force allowing the hinges 408 to easily return the friction bars back to the state of second phase or first phase operation.

The inner end 418 of hinge 408 moves inside a slot in plunger extension 406 and the opposite end of hinge 408 moves inside a slot in the end of friction block 404.

Figure 11A:
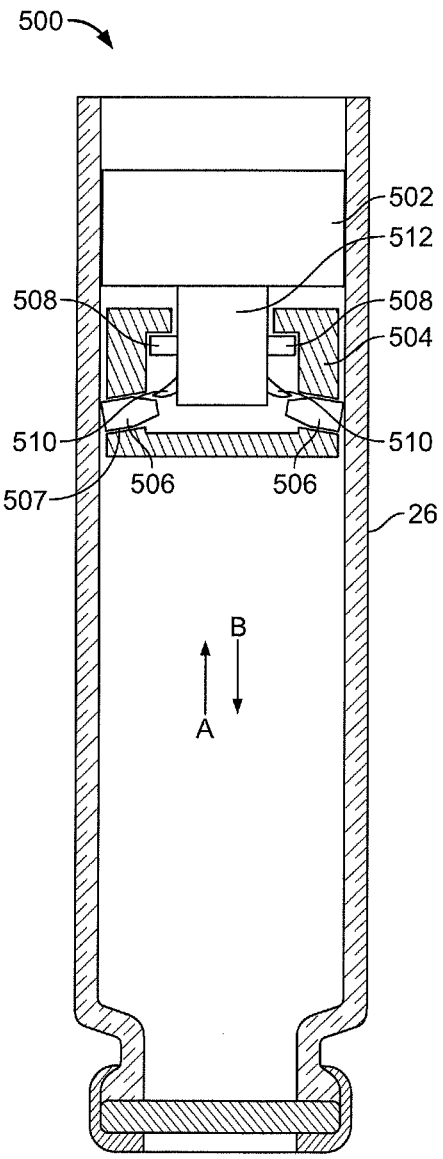
FIGS. 11A-11C are cross-sectional side views of an alternative embodiment of a multi-mode, variable flow device associated with a plunger of a syringe cartridge.
Figure 11B:
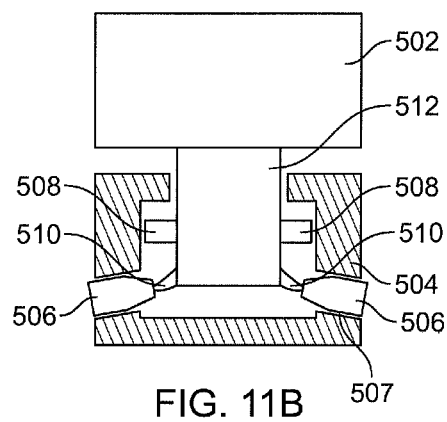
Figure 11C:
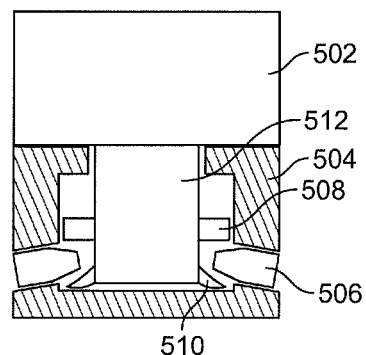

Referring to FIGS. 11A-11C, a multi-mode device 500 is attached to a cartridge plunger 502 and includes a friction unit 504, friction bars 506, first phase tabs 508, second phase tabs 510, and a plunger extension 512. The tabs 508, 510 are connected to the plunger extension 512, and the friction unit 504 is slidably received within the cartridge housing 26 and surrounds the tabs 508, 510. The friction bars 506 are located in the slots 507 within the friction unit 504. When the tabs 510 are positioned against the friction bars 506 (FIG. 11 B), the friction bars 506 are moved against the cartridge housing 26 and there is a greater resistance to sliding of the plunger 502 within the cartridge housing 26. Friction unit 504 has large holes in its upper and lower surfaces, permitting the fluid to freely flow to and from the space between it and the lower surface of plunger 502 from and to the cavity within friction unit 504 and to freely flow to and from the cavity in friction unit 504 from and to the main volume of the cartridge 26. The friction unit 504 resists its motion during all phases due to the friction it has with the cartridge housing 26.

The multi-mode device 500 defines three phases of flow. The first phase allows flow in a reverse direction, arrow A, when the operator applies a back force to the cartridge plunger 502. As the operator applies back force to the cartridge plunger 502, the first phase tabs 508 pull the friction unit 504 in the reverse direction. During the first phase, the friction bars 506 are not against the housing 26 of the cartridge 24, and the syringe has flow characteristics nearly identical to an unaltered cartridge.

Referring to FIG. 11B, the second phase allows flow in a forward direction, arrow B, when the operator applies a forward value of the force-related variable below the threshold value to the cartridge plunger 502. When the operator applies a below threshold forward value of the force-related variable to the cartridge plunger 502, the second phase tabs 510 push on the friction bars 506 pressing the friction bars 506 against the housing 26 of the cartridge 24, thereby increasing the friction of the cartridge plunger 502 and reducing the flow rate. The second phase tabs 510 are deformed and lodged against the friction bars 506 for the duration of the second phase and under a wide range of combinations of forces, impulses, and/or impacts applied to the cartridge plunger 502.

Referring to FIG. 11C, the third phase allows flow in a forward direction, arrow B, with a wide range of flow rates including a flow rate above the predetermined rate if the operator applies a forward value of the force-related variable at or above the threshold to the cartridge plunger 502. As the forward value of the force-related variable applied to the cartridge plunger 502 reaches the threshold, the second phase tabs 510 bend enough to clear the friction bars 506 and no longer apply force to the friction bars 506 such that the friction bars 506 are spaced from the housing 26 and the syringe has properties nearly identical to an unaltered cartridge.

The upper surface of each second phase tab 510 is designed to have a low coefficient of friction such that the second phase tabs 510 quickly and easily slide upward when the operator applies a negative force to the plunger 502, returning the multi-mode device 500 to its first phase of operation (FIG. 11A) from third phase operation. Likewise, multi-mode device 500 may be easily returned to first phase operation from second phase operation.

FIGS. 11D-F illustrate a version of the embodiment of FIGS. 11A-C where the braking mechanism is isolated from the anesthetic fluid. This permits a wider range of materials to be used for that mechanism. Also, the braking mechanism/cartridge occupies less volume in the cartridge.

The primary differences between this version and that illustrated in FIGS. 11A-C are that plunger extension 512a has been extended through the bottom of friction unit 504a, and a layer 509 of normal cartridge plunger diameter is affixed to the extended plunger extension 512a.

The layer 509 isolates the braking mechanism from the anesthetic fluid. The layer 509 can be used to pull back the friction unit 504a during the first phase (FIG. 11D). This eliminates the need for the tabs 508. Eliminating the tabs 508 permits a significant reduction in the length of the friction unit 504a. This reduction more than compensates for the thickness of the layer 509. The second phase is illustrated in FIG. 11E, and the third phase is illustrated in FIG. 11F.

The cartridge plunger 502a and the layer 509 define a fixed volume, so there is no need for fluid to flow in and out of this volume as the friction unit 504a moves inside of it. Holes (not shown) are provided in the friction unit 504a to permit the fluid in the volume between the friction unit 504a and the cartridge plunger 502a to flow to and from the volume between the friction unit 504a and the layer 509. The fluid can be air. If there is a potential danger of the air getting into the anesthetic liquid, the fluid can be sterilized water or more anesthetic fluid.

Similar adaptations can be made to the embodiments illustrated in FIGS. 10 and 12 to result in braking mechanisms enclosed within the cartridge plunger.

Referring to FIGS. 12A-12E, in another alternative embodiment, a multi-mode device 600 located at but not affixed to the cartridge plunger 602 includes a ring 606 attached to at least one lock 608 (three locks being shown) by posts 612. Each lock 608 includes first and second segments 620, 622, respectively, connected by a center segment 624. Mounted between the locks 608 are three ring segments 604 which can move radially inward and outward. Both ends 626, 628 of each ring segment 604 define a slot

630. The radial position of the ring segments 604 depends on the position of the lock segments 620, 622, 624 relative to the slots 630. The multi-mode device 600 defines an opening 610 for fluid flow therethrough.

In its initial state, the cartridge plunger 602 is located against the ring 606 (FIG. 12A), and the lock segments 620, 622 are positioned between the ring segments 604 such that the ring segments are held in the outward radial position, compressed and frictionally engaging the housing 26. The multi-mode device 600 defines three flow phases. The first phase allows flow in a reverse direction, arrow A, through the opening 610 when the operator applies a back force to the cartridge plunger 602. During the first phase, the cartridge plunger 602 moves in a reverse direction, arrow A, in response to the force applied by the operator (FIG. 12C), while the multi-mode device 600 remains stationary.

Figure 12A:
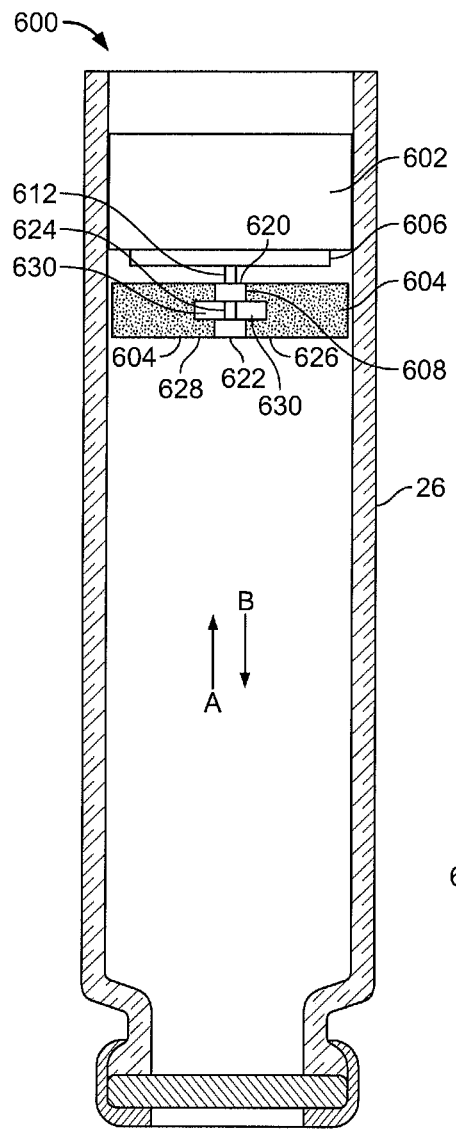
FIGS. 12A and 12C-12E are cross-sectional side views of an additional alternative embodiment of a multi-mode, variable flow device associated with a plunger of a syringe cartridge.
Figure 12B:
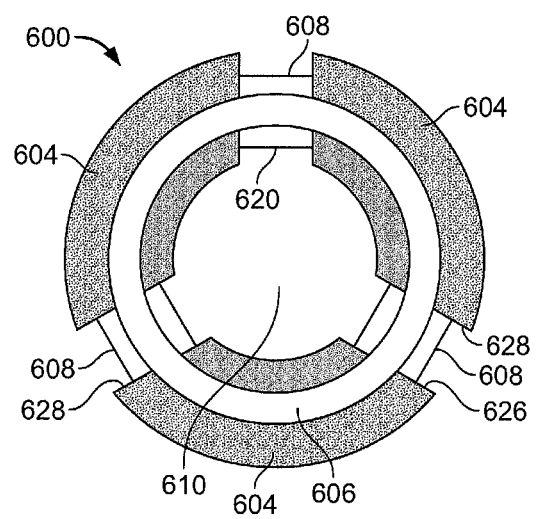
FIG. 12B is a top view of the multi-mode, variable flow device of FIGS. 12A and 12C-12E.
Figure 12C:
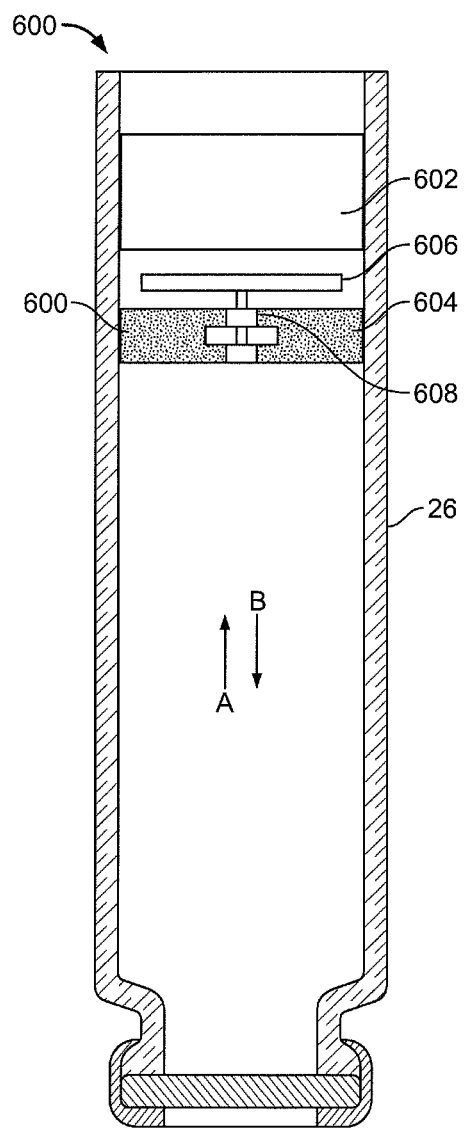
Figure 12D:
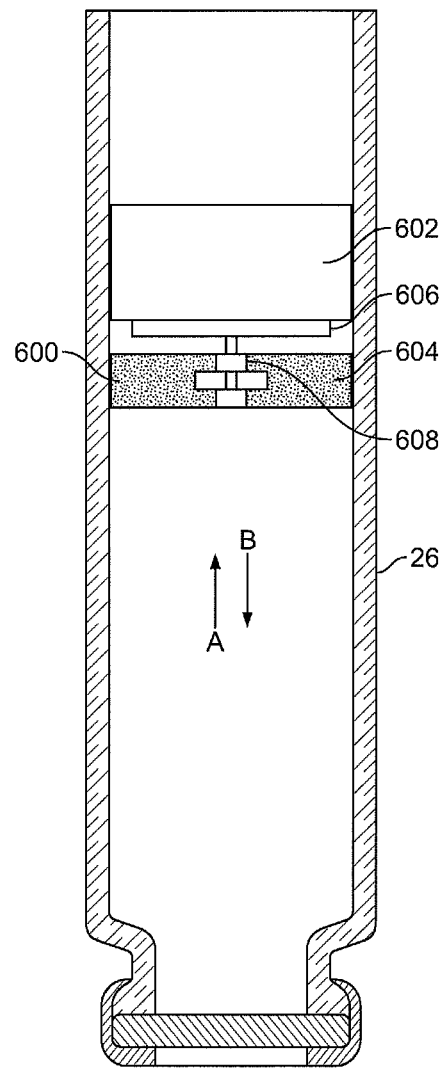

Referring to FIG. 12D, the second phase allows flow in a forward direction, arrow B, through the opening 610 when the operator applies a forward value of the force-related variable below the threshold to the cartridge plunger 602. In response to the forward force applied by the operator, the cartridge plunger 602 travels with the same properties as an unaltered cartridge until it reaches the ring 606. This permits the unrestricted return of the volume of fluid removed from the body during the first phase. When the cartridge plunger 602 reaches the ring 606 (FIG. 12A), the cartridge plunger 602 and the multi-mode device 600 travel together and the friction between the multi-mode device 600 and the housing 26 reduces the flow rate during the second phase.

Figure 12E:
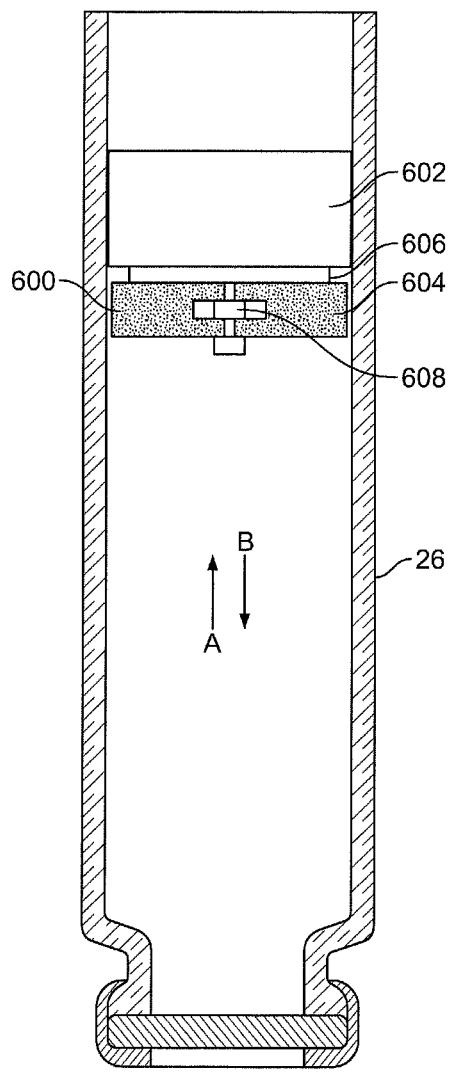

Referring to FIG. 12E, the third phase allows flow in a forward direction, arrow B, through the opening 610 with a wide range of flow rates including flow rate above the predetermined rate when the operator applies a forward value of the force-related variable at or above the threshold to the cartridge plunger 602. As the forward value of the force-related variable applied to the cartridge plunger 602 reaches the threshold, the lock segments 620, 622 are displaced reducing the force applied by the ring segments 604 on the housing 26 such that the total friction applied by the cartridge plunger 602 and the ring segments 604 is about the same as a conventional cartridge plunger. A membrane or elastic band can be used to bias the ring segments 604 inward. With the reduced friction from the ring segments 604, the syringe now has flow properties nearly identical to an unaltered cartridge.

Rather than employing a pressure-related value as the variable that controls the transition from the second phase to the third phase, the variable can be the volume fluid of delivered in the second phase. The embodiment illustrated in FIGS. 12A-12E can be configured to transition from second phase flow mode to third phase flow mode after a pre-determined volume of anesthetic has been delivered during the second phase. In this variant, the friction imposed by the friction ring 600 does not allow the multi-mode device 600 to slide during the second phase. Instead, as the plunger 602 presses on the friction ring 606, the plunger 602 causes the lock segments 620 and 622 to slide against the ring segments 604, until the plunger 620 goes into the slot 630 and the lock segment 622 goes into the volume of the cartridge. The lengths of the lock segments 620, 622 and their interface with the ring segments 604 are configured such that the predetermined second phase volume is dispensed before the transition to the third phase.

Likewise, the embodiment illustrated in FIGS. 11A-11C can be configured to transition from the second phase flow mode to the third phase flow mode after the delivery of a pre-determined volume of anesthetic. In this variant, the force of the second phase tabs against the friction bars prevents movement of friction unit 504 during the second phase. Instead, the second phase tabs 510 slide along the inner surface 514 of the friction bars 506. That surface 514 on each friction bar 506 is long enough in the direction of the length of the cartridge such that the second phase tabs 510 remain engaged until the pre-determined volume of second phase anesthetic is delivered. When the second phase tabs 510 slide beyond that surface 514, the unit enters the third phase.

Alternatively, the embodiments illustrated in FIGS. 11A-11C and 12A-12E, can be configured to transition from second phase flow mode to third phase flow mode after the delivery of a pre-determined volume of anesthetic or by reaching a value of a force-related variable at, or above, a threshold value, whichever occurs first during a given second phase operation.

Figure 13:
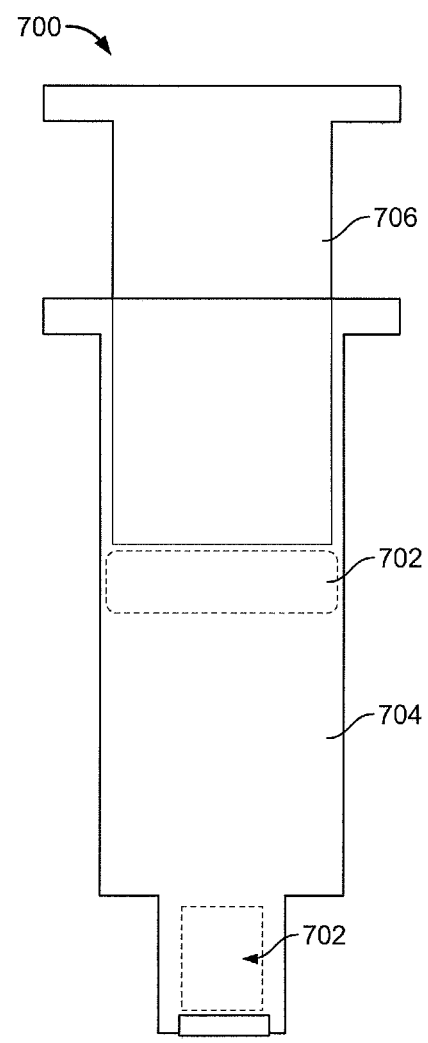
FIG. 13 is a syringe barrel including a multi-mode, variable flow device.

Rather than incorporating a multi-mode device in a cartridge, a multi-mode device such as any of the embodiments described above can be incorporated into a syringe having a standard barrel and plunger arrangement. Referring to FIG. 13, a syringe 700 includes a barrel 704 for containing a medium, a plunger 706 for applying a force to the medium, and a multi-mode device 702 incorporated within the barrel 704 and/or the plunger 706 defining at least two flow rates that differ in response to the value of a variable, for example, pressure. The multi-mode device 702 may be any one of the multi-mode devices described with reference to FIGS. 1-12.

Figure 14:
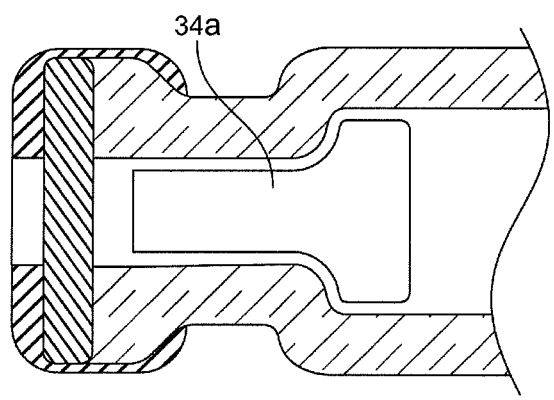
FIG. 14 is a cross-sectional side view of an alternative configuration of the multi-mode, variable flow device of FIG. 2.

The multi-mode device can have a shape other than cylindrical. For example, referring the FIG. 14, a variable control device 34*a* flares proximally to mirror the shape of the inner wall of the cartridge.

Figure 15A:
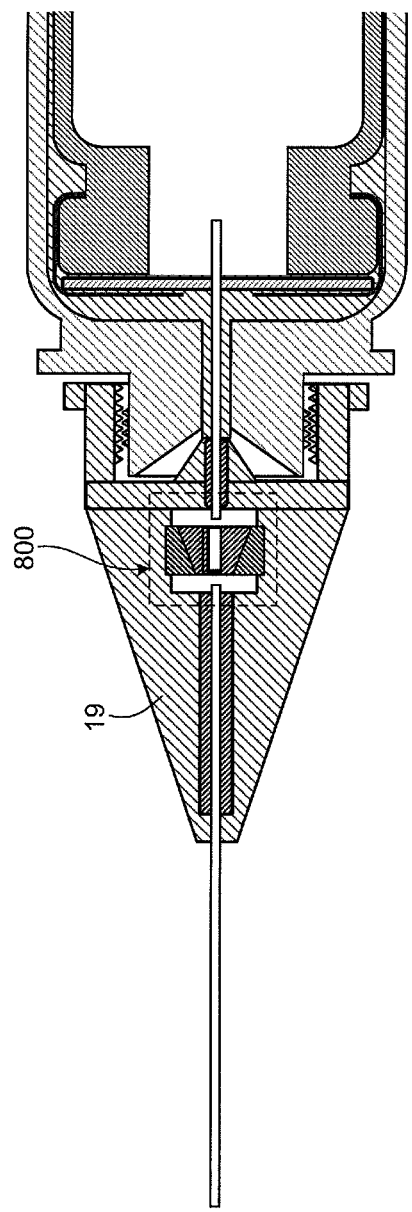
FIG. 15A is a cross-sectional side view of an alternative embodiment of a multi-mode, variable flow device associated with a needle assembly of a syringe.

Rather than positioning the multi-mode device in a cartridge, a multi-mode device can be positioned within the needle hilt 19. For example, referring to FIGS. 15A-15D, a multi-mode device 800 includes a flow body 802 sized to be received within a groove 23 of a bore 21 of the needle hilt 19. The flow body 802 defines first and second through holes 806 and 808 extending from a front, proximal face 804 to a back, distal face 810 of the flow body 802 for delivery of anesthetic therethrough perpendicular to the faces. Four cut portions 812 form four lines on the front face 804 (FIG. 15C) with solid corners and extend through the flow body 802 to form a square cut out on the distal face 810 (FIG. 15D).

The cut portions 812 are at an acute angle 813, e.g., 45-70 degrees, from the back face 810. A removable plug 809 is located at the distal end 815 of the second through hole 808. The plug 809 can be, e.g., a region of the flow body 802 left when the second through hole 808 is created. Alternatively, the plug 809 can be, e.g., an insert fixed within the second through hole 808 or a seal made by heating the region of the back face 810 surrounding the opening of the second through hole 808.

The plug 809 covers the opening of the through hole 808 at the back face 810 until a net forward, B, pressure-related variable across the front face 804 reaches a threshold. Once the net forward pressure-related variable across the front face 804 is at or above the threshold, the plug is removed, enabling flow through the second through hole 808. The diameter of the first through hole 806 depends on the maximum acceptable forward flow rate at the site of injection during the second phase. The diameter of the second through hole 808 is about the same as or greater than the inner diameter of the needle of needle assembly 18.

The multi-mode device 800 defines three flow paths. The first flow path is in a backward direction, arrow A, through the cut portions 812 and the first through hole 806 when the operator applies a back force to the cartridge plunger 30 resulting in net back pressure across the flow body 802. The second flow path is through only the first through hole 806 in a forward direction, arrow B, when a variable, here the operator applied forward value of a force-related variable placed on the cartridge plunger 30 resulting in a pressure-related variable across the flow body 802, is below a threshold. In the second flow path, there is no flow through the cut portions 812 as the forward pressure-related variable across the flow body 802 closes the cut portions 812 due to the angle of the cut portions 812 into the flow body 802. The third flow path is through the first through hole 806 and the second through hole 808, which begins when the operator applies a forward value of a force-related variable on the front face 804 of the cartridge plunger 30 resulting in a pressure-related variable across the flow body 802 at or above the threshold resulting in removal of the plug 809. For example, the plug 809 is removed when the pressure-related variable across the front face 804 of the flow body 802 is at, for example, 150 to 350 kPa.

Figure 16:
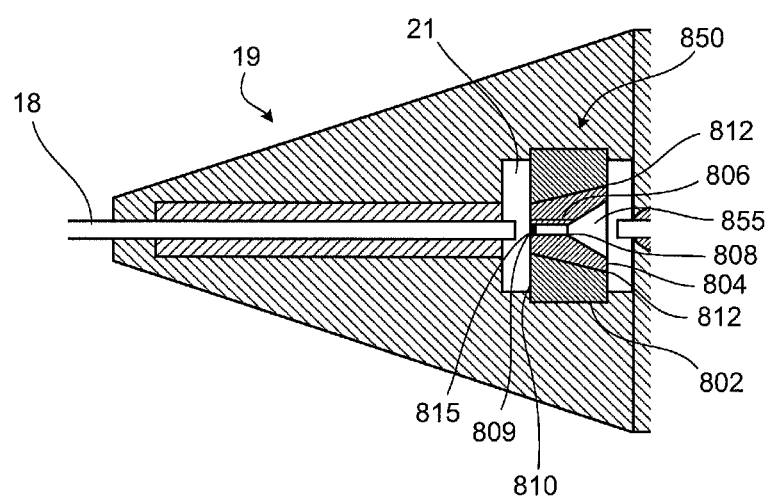
FIG. 16 is a cross-sectional side view of an alternative embodiment of a multi-mode, variable flow device associated with a needle assembly of a syringe.

Referring to FIG. 16, rather than the through hole 808 having a constant diameter across the flow body 802, a multi-mode device 850 received within the needle hilt 19 includes a pyramidal shaped bore 855 extending from the front face 804 that aids in limiting flow through the cut portions 812 in a forward direction, B. When a forward pressure-related variable is applied across the front face 804 of the multi-mode device 850, the pyramidal shaped bore 855 results in a more perpendicular force being applied to the cut portions 812, keeping the cut portions 812 closed.

Figure 17A:
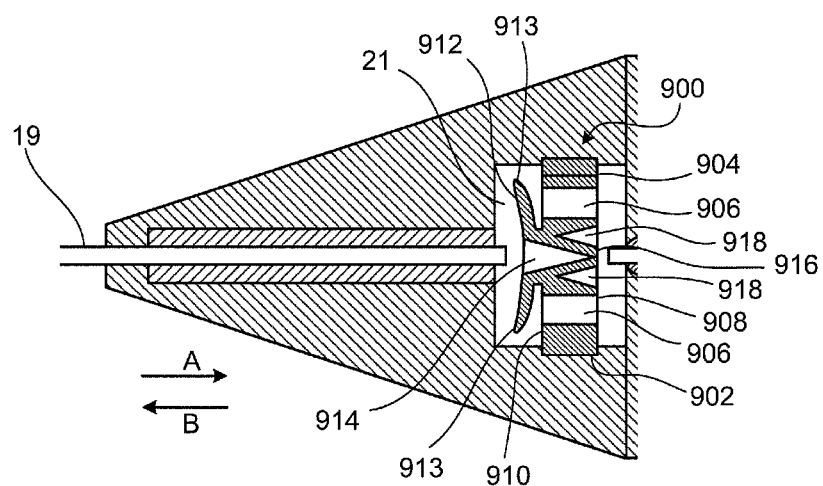
FIGS. 17A, 17D, and 17E are cross-sectional side views of an alternative embodiment of a multi-mode, variable flow device associated with a needle assembly of a syringe.
Figures 17B, 17C:
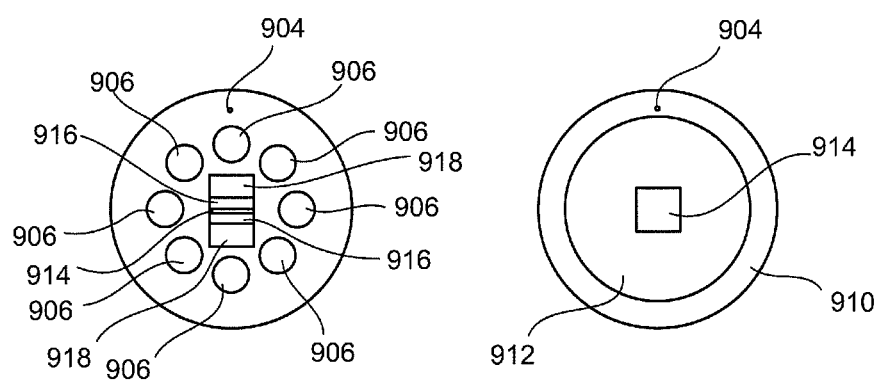
FIG. 17B is a proximal view of the multi-mode, variable flow device of FIG. 17A, 17D, and 17E.
FIG. 17C is a distal view of the multi-mode, variable flow device of FIG. 17A, 17D, and 17E.
Figure 17D:
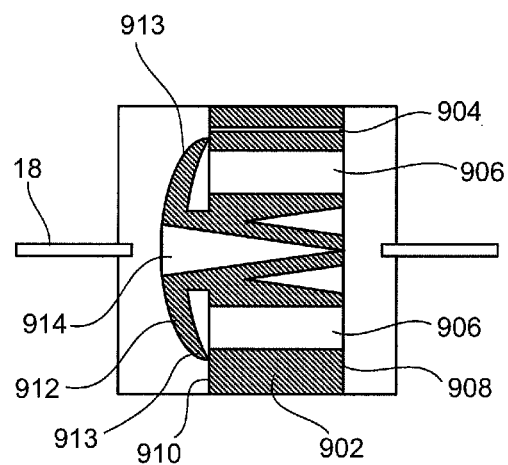

Referring to 17A-17E, in another alternative embodiment, a multi-mode device 900 includes a flow body 902 that has holes through which flow is controlled by an annular rim 912. Flow body 902 defines a first through hole 904 and a plurality, e.g., eight, second through holes 906 extending from a front, proximal face 908 to a back, distal face 910 of flow body 902 for delivery of anesthetic therethrough. Extending from the back face 910 is the annular rim 912 that acts as a bi-stable valve covering the second through holes 906 (FIG. 17D). The annular rim 912 includes a one-way valve 914 extending through the center of the annular rim 912 and through flow body 902 to the front face 908 of the flow body 902 that allows flow in a backward, arrow A, direction.

Figure 17E:
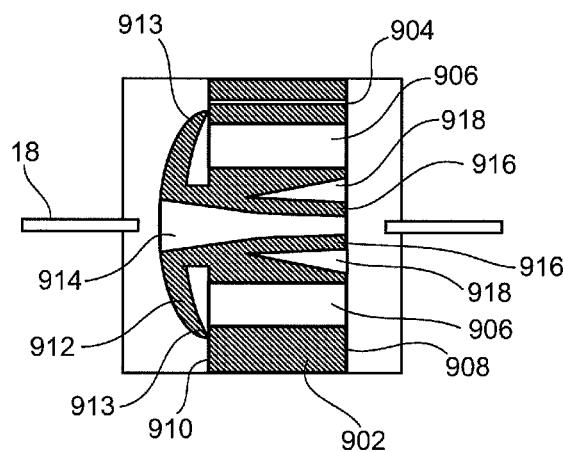

Before a force is applied to the cartridge plunger 30, the annular rim 912 is curved such that outer regions 913 of the annular rim 912 abut against the back face 910, e.g., the annular rim 912 is stably closed, to restrict flow through the second through holes 906 (FIG. 17D). When the operator applies back force to the cartridge plunger 30, a first flow path is created through the one-way valve 914 and the first through hole 904 in a backward direction, arrow A. That is, fluid flowing from the distal region of the one-way valve 914 forces the proximal regions 916 of the one-way valve 914 into wedge shaped bores 918 extending from the front face 908, thereby opening the one-way valve 914, as illustrated in FIG. 17E. When the back force ceases, the proximal region of tie one-way valve 914 closes, as illustrated in FIG. 17D. When the operator applies a forward force to the cartridge plunger 30 that is below a threshold pressure, the outer regions 913 of the annular rim 912 are maintained against the back face 910 to substantially prohibit the flow through the plurality of second through holes 906, and flow occurs through the second flow path defined by the first through hole 904 in a forward direction, arrow B, as illustrated in FIG. 17D. When the operator applies a forward force to the cartridge plunger 30 that is at or above the threshold, the outer regions 913 of the annular rim 912 move away from the face 910, e.g., the annular rim 912 is stably open, allowing flow through the second through holes 906, in addition to the first through hole 904, as illustrated in FIG. 17A. To again restrict flow through the second through holes 906, the operator applies back force to the cartridge plunger 30 so that the outer regions 913 of the annular rim 912 move back against the face 910. This returns the multi-mode device 900 to a state where a reverse plunger force will result in a first phase fluid flow and a below threshold forward cartridge force will result in a second phase fluid flow.

Referring to 18A-18D, in another alternative embodiment, a multi-mode device 1000 includes a ball valve 1001 defining a chamber 1002 in the needle hilt 19. The multi-mode device 1000 includes a flexible disk 1004, back, proximal cushion 1006, front, distal cushion 1007, and a flow restriction member 1008. The flexible disk 1004 includes a first through hole 1009 having a diameter smaller than the diameter of the flow restriction member 1008 and a second through hole 1012. The chamber 1002 is defined to impede distortion of the flexible disk 1004 towards the distal end of the chamber 1002, but not impede distortion of the flexible disk 1004 in the opposite direction towards the proximal end of the chamber 1002.

Figure 18A:
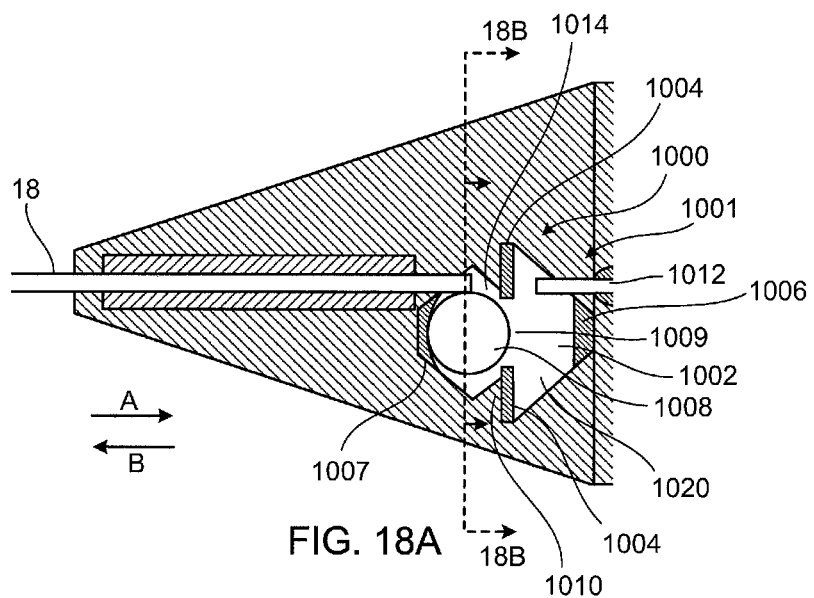
FIGS. 18A, 18C, and 18D are cross-sectional side views of an alternative embodiment of a multi-mode, variable flow device associated with a needle assembly of a syringe.
Figure 18B:
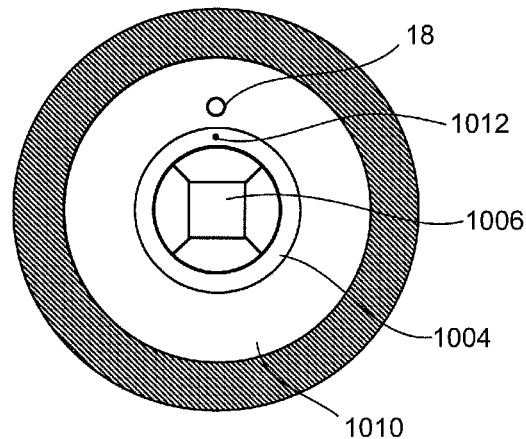
FIG. 18B is a cross-sectional view taken along line 18B-18B of FIG. 18A without a flow restriction member.
Figure 18C:
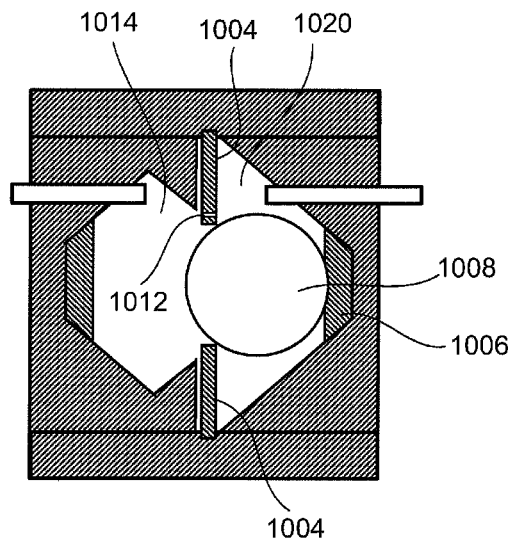
Figure 18D:
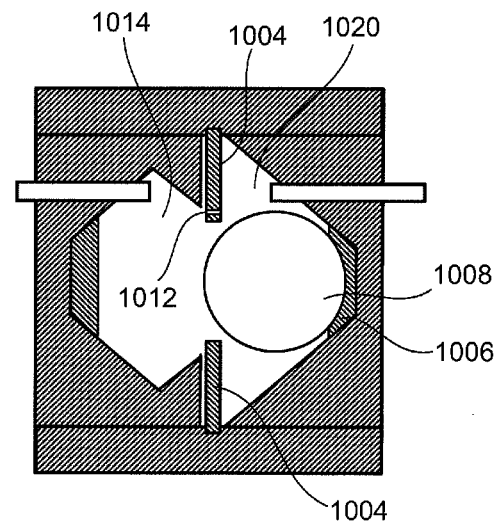

Before force is first applied to the cartridge plunger 30, flow restriction member 1008 is held against the back cushion 1006 by the flexible disk 1004 (FIG. 18C). The flow restriction member 1008 covers the first through hole 1009 so that flow is restricted through the first through hole 1009. When the operator applies back force to the cartridge plunger 30, the fluid pressure applied to the flow restriction member 1008 in the backward direction, arrow A, forces the flow restriction member 1008 against the back cushion 1006, which distorts, allowing the flow restriction member 1008 to move apart from the flexible disk 1004 such that the flow restriction member 1008 does not completely cover the first through hole 1009 (FIG. 18D) and a flow path is created through the first through hole 1009 and the second through hole 1012. When the back force ceases, the flow restriction member 1008 returns to its initial position and covers the first through hole 1009, as illustrated in FIG. 18C. When the operator applies a forward, arrow B, force to the cartridge plunger 30 that is below a threshold, a second flow path in the forward direction is created through the second through hole 1012. The flexible disk 1004 also distorts due to the pressure applied to it by the flow restriction member 1008, but the distortion is not great enough to allow the flow restriction member 1008 to pass through the first through hole 1009. When the operator applies a forward force to the cartridge plunger 30 that is at or above the threshold, the flexible disk 1004 distorts to allow the flow restriction member 1008 to pass through the first through hole 1009 into the distal region 1014 of the chamber 1002, as illustrated in FIG. 18A. The fluid pressure applied to the flow restriction member 1008 in the forward direction, B, forces the flow restriction member 1008 against the front cushion 1007, which distorts, allowing the flow restriction member 1008 to move apart from the flexible disk 1004 such that the flow restriction member 1008 does not completely cover the first through hole 1009 (FIG. 1 8A). A third flow path is thus created through the first through hole 1009 and the second through hole 1012 in the forward direction, B.

To again restrict flow through the first through hole 1009, the operator ceases the forward force to the cartridge plunger 30 so that the flow restriction member 1008 covers the first through hole 1009. In addition, to return the multi-mode device 1000 to a state where a below threshold forward cartridge plunger force results in the second phase response mode and a reverse cartridge plunger force results in the first phase fluid flow, the operator applies back force to the cartridge plunger 30 so that the flow restriction member 1008 returns to a proximal region 1020 of the chamber 1002 (FIG. 18C). Less pressure is required to distort the flexible disk 1004 toward the proximal end of the chamber 1002 because, as discussed above, the chamber 1002 is defined not to impede the flexible disk 1004 toward the proximal end of the chamber 1002.

Figure 19A:
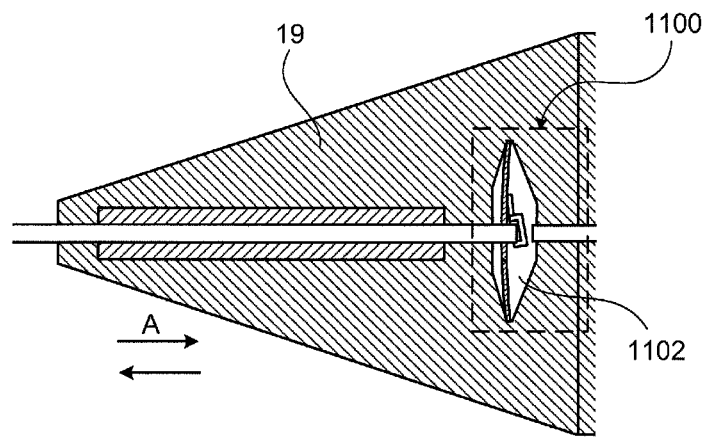
FIG. 19A is a cross-sectional side view of an alternative embodiment of a multi-mode, variable flow device associated with a needle assembly of a syringe.
Figure 19B:
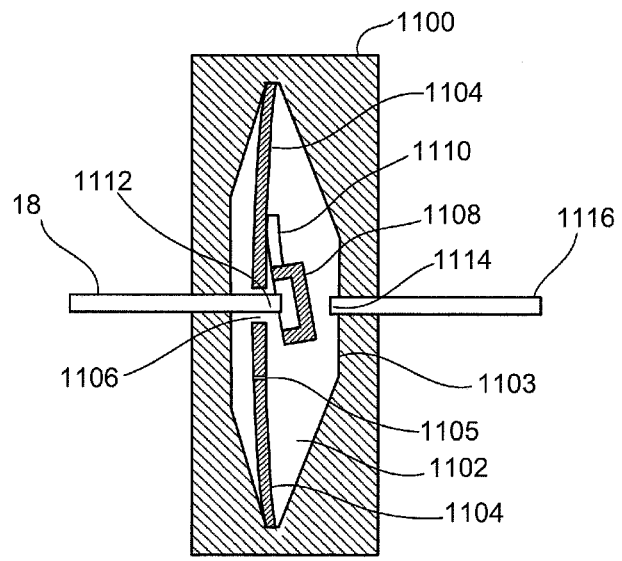
FIGS. 19B, 19C, and 19D are exploded side views of the multi-mode, variable flow device of FIG. 19A.

Referring to FIGS. 19A and 19B, rather than the ball valve 1001, a multi-mode device 1100 includes a bi-stable valve 1008 in a chamber 1102 in the needle hilt 19 for delivery of anesthetic therethrough. Within the chamber 1102 is a membrane 1104 that defines a first through hole 1105 and a second through hole 1106. The flow of anesthetic through the second through hole 1106 can be blocked or unblocked by a bi-stable valve 1108. The bi-stable valve 1108 is attached to the membrane 1104 by a hinge 1110. The bi-stable valve 1108 is controlled by the proximal end 1112 of the needle assembly 18 and the proximal wall 1103 of the chamber 1102. The bi-stable valve 1108 can move to a non-stable partially open position toward the proximal wall 1103 under a back pressure resulting from an applied back force. The stable open position of the bi-stable valve 1108 is achieved, for example, by an elastic band 1114 (FIG. 1 9D) extending between the hinge 1110 and the bi-stable valve 1104.

Figure 19C:
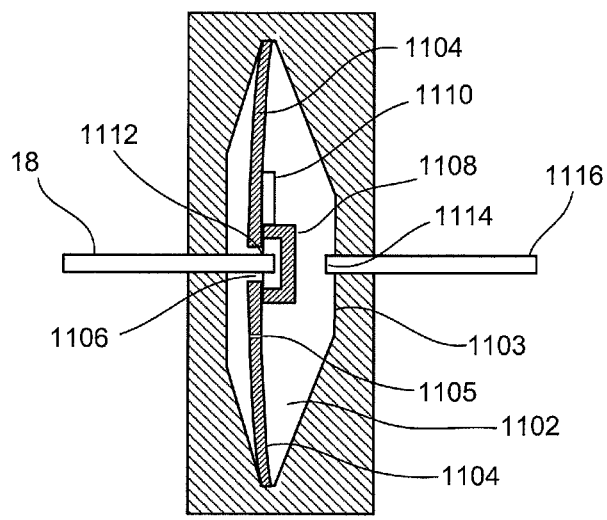
Figure 19D:
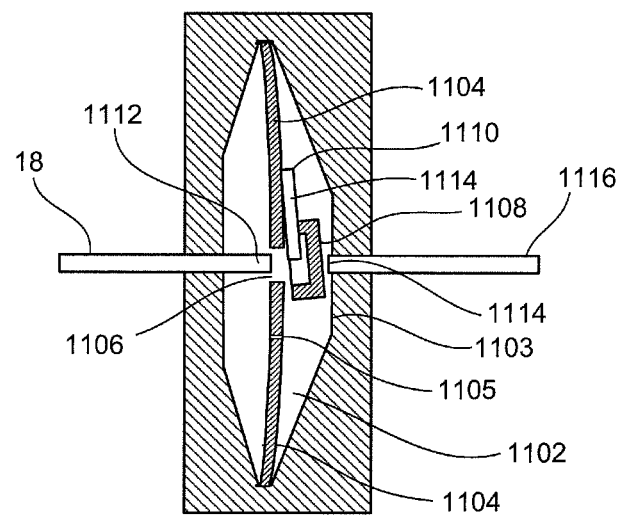

Before force is first applied to the cartridge plunger 30, the bi-stable valve 1108 is closed. When the operator applies back force to the cartridge plunger 30, sufficient for it to move, a first flow path is created through the second through hole 1106 as the bi-stable valve 1108 is in its partially open position (FIG. 19D), that is, the valve has moved toward or up against the proximal wall 1103 but short of its stable open position. When the back force ceases, the pressure differential across membrane 1104 is reduced due to flow in a backward direction, arrow A, and the bi-stable valve 1108 returns to its closed position (FIG. 19C). When the operator applies forward force to the cartridge plunger 30 that is below a threshold pressure, the bi-stable valve 1108 remains closed and the second flow path is through the first through hole 1105 (FIG. 19C). When the operator applies a forward force to the cartridge plunger 30 resulting in a forward value of a variable related to the pressure differential across membrane 1104 that is at or above the threshold, the membrane 1104 distorts and moves the bi-stable valve 1108 against the proximal end 1112 of the needle assembly 18 to allow flow through the second through hole 1106. The proximal end 1112 of the needle assembly 18 pushes the bi-stable valve 1108 to a stably open mode. Because the bi-stable valve 1108 is stably open, it remains open after the pressure differential across membrane 1104 is lessened and the membrane 1104 returns to its original position. To close the bi-stable valve 1108, the operator applies a negative force to the cartridge plunger 30 resulting in a negative value of a variable related to the pressure differential across membrane 1104 such that the membrane 1104 moves the bi-stable valve 1108 against the proximal wall 1103. The proximal wall 1103 pushes the bi-stable valve 1108 closed. This returns the multi-mode device 1100 to a state where a below threshold forward cartridge plunger force results in a second phase response mode and a reverse cartridge plunger force results in a first phase fluid flow.

The burst of flow that occurs from triggering the third phase can be tailored by designing the bi-stable valve 1108 to open at a pre-defined rate. The bi-stable valve 1108 can be designed to open slowly to reduce the trigger flow, or the bi-stable valve 1108 can be completely removed or altered if a microfluidic circuit is used.

A number of embodiments of the invention have been described. Nevertheless, it will be understood that various modifications may be made without departing from the spirit and scope of the invention. For example, referring to the embodiment of FIGS. 3A-3D, to alter the threshold pressure for the transition from the second phase to the third phase, the thickness of the membrane 58 can be varied with respect to its distance from the location where the back of the needle assembly penetrates the membrane. At the location of penetration, a thinner membrane 58 is more easily penetrated and is more likely to tear, whereas a thicker membrane 58 is more likely to be penetrated without tearing. In variants where the membrane 58 is designed for penetration without tearing, a backward force on the plunger can cause the back of the needle to be retracted from the membrane 58. This will cause a transition back to the second phase. Outside the location of penetration, the thinner the membrane 58, the more the membrane distorts due to the pressure differential across membrane 58 resulting from the force applied by the cartridge plunger 30 and the thicker the membrane 58, the less the membrane distorts due to the pressure differential across membrane 58 resulting from the force applied by the cartridge plunger 30.

Rather than the seal 32 being a separate component from the multi-mode device, as shown in FIG. 2, the seal can be incorporated into the distal end of the multi-mode device.

Rather than the first through hole 806 of FIGS. 15A-15D and 16 being located through a solid region of the flow body 802 perpendicular to the front face 804 or the back face 810 and parallel to the second through hole 808, the first through hole 806 can be located along one or more of the cut portions 812. Similarly, rather the second through hole 808 of FIGS. 15A-C and 16 being located through a solid region of the flow body 802 perpendicular to the front face 804 or the back face 810, the second through hole 808 can be located along one or more of the cut portions 812. Alternatively, the first through hole 806 can be replaced by a through hole through the plug 809. The diameter of the through hole through the plug 809 can be the same as or different from the diameter of the first through hole 806.

Rather than the plug 809 of FIGS. 15A-C being located at the distal end 815 of the flow body 802, the plug 809 can be located at the opposite, proximal end 816 of the flow body 802, covering the opening of the through hole 808 at the front face 804.

Rather than the second through hole 1012 being defined through the flexible disk 1004, the second through hole 1012can also be defined through the flow restriction member 1008. Although a spherical shape is shown for the flow restriction member 1008, another shape, such as an ellipsoid shape.

Rather than including the back, proximal cushion 1006 and the front, distal cushion 1007 in the a multi-mode device 1000, the flow restriction member 1008 can be made of a resilient material. For example, the flow restriction member 1008 can distort if the pressure applied to the flow restriction member 1008 is at or greater than a threshold to allow the flow restriction member 1008 to move apart from the flexible disk 1004 such that the flow restriction member 1008 does not completely cover the first through hole 1009.

Rather than the proximal wall 1103 of FIGS. 19A-19D controlling the bi-stable valve 1108, a distal end 1114 of needle assembly 1116 can control the bi-stable valve 1108.

A proximal end of the needle assembly 1116 can penetrate the seal 32 of the cartridge 24 to allow flow into and out of the cartridge 24.

Although the multi-mode devices 34, 300, 100, and 200 have been explained to be incorporated in the cartridge 24, they can also be incorporated in the needle hilt 19. Similarly, although the multi-mode devices 800, 850, 900, 1000, and 1100 have been explained to be incorporated in the needle hilt 19, they can also be incorporated in the cartridge 24.

The multi-mode devices described above may be made from any elastomer, such as a thermoplastic or thermoset elastomer. Examples of suitable elastomers include Santoprene, ethylene propylene diene M-class polypropylene rubber (EPDM-PP), ethylene propylene diene M-class rubber (EPDM), or silicone.

The multi-mode device can include a needle guide in the chamber that receives the needle assembly 18 to direct the final location of the sharp tip 64 of the needle assembly 18 to improve reproducibility.

In addition to the embodiments described above, the multi-mode device can be built into any part of the syringe outside of the cartridge and needle assembly.

Accordingly, other embodiments are within the scope of the following claims.

What is claimed is:

1. A multi-mode, syringe device, comprising: a body sized for placement within a syringe assembly, the syringe assembly including a plunger assembly, the body defining three flow paths, the body configured to form flow in only a first direction through a first flow path of the three flow paths, the body configured to automatically form flow below a predetermined rate in a second direction opposite the first direction in response to a variable having a value below a threshold through a second flow path of the three flow paths, the body configured to automatically form flow in the second direction at a rate higher than the predetermined rate in response to the variable reaching a value at or above the threshold through a third flow path of the three flow paths, wherein the variable is a force in the second direction applied to the plunger assembly of the syringe assembly.

2. The multi-mode, syringe device of claim 1, wherein the second and third flow paths are configured to have flow rates that differ in response to the same value of the variable.

3. The multi-mode, syringe device of claim 1, wherein the body defines a first through hole forming the first flow path, a second through hole forming the second flow path, and a third through hole forming the third flow path.

4. The multi-mode, syringe device of claim 3, further comprising a first valve located at an end of the first through hole, a second valve located at an end of the second through hole, and a third valve located at an end of the third through hole.

5. The multi-mode, syringe device of claim 3, wherein the first through hole is smaller than the second through hole, and the second through hole is smaller than the third through hole.

6. The multi-mode, syringe device of claim 1, wherein the body defines a first through hole forming the second flow path, and at least one second through hole forming the third flow path.

7. The multi-mode, syringe device of claim 6, wherein the first through hole is smaller than the second through hole.

8. The multi-mode, syringe device of claim 6, further comprising a flow restriction member located at an end of the second through hole, wherein the flow restriction member is configured to be removed in response to the variable reaching a value at or above the threshold.

9. The multi-mode, syringe device of claim 6, wherein the body defines multiple second through holes forming the third flow path.

10. The multi-mode, syringe device of claim 6, wherein the body defines a one-way valve forming the first flow path, the one-way valve forming flow only in the first direction.

11. The multi-mode, syringe device of claim 1, wherein the body is configured to be received within a needle hilt of the syringe assembly.

12. The multi-mode, syringe device of claim 1, wherein the body is configured to be received within a housing of the syringe assembly.

13. The multi-mode, syringe device of claim 1, wherein the body is configured to be attached to a plunger of the syringe assembly.

14. A syringe assembly, comprising: a syringe including a plunger assembly; and a body sized for placement within the syringe, the body defining three flow paths, the body configured to form flow in only a first direction through a first flow path of the three flow paths, the body configured to automatically form flow below a predetermined rate in a second direction opposite the first direction in response to a variable having a value below a threshold through a second flow path of the three flow paths, the body configured to automatically form flow in the second direction at a rate higher than the predetermined rate in response to the variable reaching a value at or above the threshold through a third flow path of the three flow paths, wherein the variable is a force in the second direction applied to the plunger assembly of the syringe.

15. A multi-mode, syringe device comprising:
a body sized for placement within a syringe assembly, the syringe assembly including a plunger assembly and the body including:
a first flow path including a flow regulation assembly configured to permit flow in only a first direction through the first flow path,
a second flow path including a flow regulation assembly configured to automatically restrict flow through the second flow path below a predetermined rate in a second direction opposite the first direction in response to a variable having a value below a threshold, and
a third flow path including a flow regulation assembly configured to automatically permit flow through the third flow path in the second direction at a rate higher than the predetermined rate in response to the variable reaching a value at or above the threshold,
wherein the variable is a force in the second direction applied to the plunger assembly of the syringe.

16. The multi-mode, syringe device of claim 15, wherein the flow regulation assembly of the second flow path and the flow regulation assembly of the third flow path together comprise a single valve configured to open a first amount in response to the variable having a value below the threshold and to open a second amount greater than the first amount in response to the variable reaching a value at or above the threshold.

* * * * *